US012797630B2

(12) United States Patent
Davies-Smith et al.

(10) Patent No.: US 12,797,630 B2
(45) Date of Patent: *Nov. 17, 2026

(54) ORAL TREATMENT DEVICE AND RELATED METHODS

(71) Applicant: Colgate-Palmolive Company, New York, NY (US)

(72) Inventors: Leighton Davies-Smith, Lebanon, NJ (US); Christopher Randall Zaic, Cranbury, NJ (US)

(73) Assignee: Colgate-Palmolive Company, New York, NY (US)

( * ) Notice: Subject to any disclaimer, the term of this patent is extended or adjusted under 35 U.S.C. 154(b) by 952 days.

This patent is subject to a terminal disclaimer.

(21) Appl. No.: 17/986,148

(22) Filed: Nov. 14, 2022

(65) Prior Publication Data

US 2023/0149730 A1 May 18, 2023

Related U.S. Application Data

(60) Provisional application No. 63/280,181, filed on Nov. 17, 2021.

(51) Int. Cl.
*A61N 5/06* (2006.01)

(52) U.S. Cl.
CPC .... *A61N 5/0613* (2013.01); *A61N 2005/0606* (2013.01); *A61N 2005/0626* (2013.01); *A61N 2005/0663* (2013.01)

(58) Field of Classification Search
CPC ..... A61C 19/003; A61C 19/063; A61C 19/06; A61C 19/066; A61N 5/06;
(Continued)

(56) References Cited

U.S. PATENT DOCUMENTS 5,174,284 A * 12/1992 Jackson ............ A61M 16/0493 128/200.26
5,690,486 A 11/1997 Zigelbaum
(Continued)

FOREIGN PATENT DOCUMENTS

CN 105125311 12/2015
CN 110575621 12/2019
(Continued)

OTHER PUBLICATIONS

International Search Report and the Written Opinion of the International Searching Authority issued in International Application PCT/US2022/049757 mailed Apr. 17, 2023.

*Primary Examiner* — Heidi M Eide
*Assistant Examiner* — Lina Faraj

(57) ABSTRACT

An oral treatment device and a method of using the same. The oral treatment device includes an intraoral mouthpiece configured for placement into a mouth of a user. The intraoral mouthpiece includes an arcuate wall having a front surface and a bite platform extending from the front surface. Furthermore, there is an alignment feature located on the bite platform to facilitate consistent positioning of the intraoral mouthpiece within the user's mouth in a repeatable manner. The alignment feature may have a top surface that is inclined upwardly moving in a direction away from the front surface of the arcuate wall. The intraoral mouthpiece may also include a color measurement sensor for obtaining a color measurement of a tooth of the user.

19 Claims, 13 Drawing Sheets

(58) Field of Classification Search
CPC .... A61N 2005/0628; A61N 2005/0652; A61N 2005/0654; A61N 5/0603; A61N 2005/0606; A61N 2005/0662
See application file for complete search history.

(56) References Cited

U.S. PATENT DOCUMENTS

| | | | | |
|---|---|---|---|---|
| 6,976,841 | B1 | 12/2005 | Osterwalder | |
| 7,156,656 | B2 | 1/2007 | Duret | |
| 7,826,728 | B2 | 11/2010 | Konno et al. | |
| 8,040,514 | B2 | 10/2011 | Kobayashi | |
| 8,672,677 | B1 | 3/2014 | Kim | |
| 8,940,033 | B2 | 1/2015 | Dwyer et al. | |
| 9,622,841 | B2 | 4/2017 | Ajiki et al. | |
| 9,636,198 | B2 | 5/2017 | Kodama | |
| 9,839,500 | B2 | 12/2017 | Flyash et al. | |
| 10,369,375 | B2 | 8/2019 | Demarest et al. | |
| 10,398,894 | B2 | 9/2019 | Johansson et al. | |
| 10,870,014 | B2 | 12/2020 | Demarest et al. | |
| 10,893,924 | B2 | 1/2021 | Demarest et al. | |
| 11,040,218 | B2 | 6/2021 | Bloch et al. | |
| 11,141,254 | B2 | 10/2021 | Chapman et al. | |
| 2005/0048444 | A1 | 3/2005 | Creamer | |
| 2008/0233541 | A1 | 9/2008 | De Vreese et al. | |
| 2010/0201986 | A1* | 8/2010 | Inglese | G01J 3/02 356/407 |
| 2012/0009540 | A1 | 1/2012 | Kawa | |
| 2012/0231420 | A1 | 9/2012 | Wong et al. | |
| 2013/0045457 | A1 | 2/2013 | Chetiar et al. | |
| 2013/0089829 | A1 | 4/2013 | Boutoussov et al. | |
| 2014/0080082 | A1* | 3/2014 | Lowe | A61C 19/003 433/6 |
| 2017/0231735 | A1 | 8/2017 | Young | |
| 2018/0036164 | A1 | 2/2018 | Bryan | |
| 2018/0125627 | A1 | 5/2018 | Mounce | |
| 2019/0029564 | A1 | 1/2019 | Peru et al. | |
| 2019/0314639 | A1 | 10/2019 | Demarest et al. | |
| 2019/0388205 | A1 | 12/2019 | Whitney et al. | |
| 2020/0230432 | A1 | 7/2020 | Jablow | |
| 2021/0068936 | A1 | 3/2021 | Brawn et al. | |

FOREIGN PATENT DOCUMENTS

| | | |
|---|---|---|
| CN | 211301799 | 8/2020 |
| JP | 2018-512906 | 5/2018 |
| KR | 101396086 | 5/2014 |
| KR | 200482369 | 1/2017 |
| KR | 101865714 | 7/2018 |
| KR | 20210067560 | 6/2021 |
| WO | 2015/056034 | 4/2015 |
| WO | 2019/245945 | 12/2019 |
| WO | 2020/033221 | 2/2020 |
| WO | 2020/077480 | 4/2020 |
| WO | 2021/067345 | 4/2021 |

* cited by examiner

ORAL TREATMENT DEVICE AND RELATED METHODS

CROSS-REFERENCE TO RELATED APPLICATIONS

The present application claims priority to U.S. Provisional Patent Application Ser. No. 63/280,181, filed Nov. 17, 2021, the entirety of which is incorporated herein by reference.

BACKGROUND

Tooth whitening is an increasingly popular treatment and dentists and patients alike are searching for techniques that are both convenient and comfortable while also being effective. Typically, to whiten a user's teeth a composition containing hydrogen peroxide is applied to the teeth and allowed to remain in contact with the teeth to be bleached for a period of time. Current systems are available that allow a user to apply radiation or light to the surfaces of the teeth that are pre-coated with the whitening composition to enhance the effectiveness of the whitening composition. However, users have a difficult time detecting whether the tooth whitening treatment is effective because a user is only able to detect a color difference that exceeds a threshold, known as the just noticeable difference. Furthermore, people generally do not have good color recall, and thus cannot remember what their teeth look like from one day to the next as the color of their teeth changes as a result of a whitening treatment or protocol. Thus, a need exists for an oral treatment device that can detect tooth color for purposes of providing a user with an indication of a color change occurring over time as a result of multiple uses of the oral treatment device.

BRIEF SUMMARY

The present invention is directed to an oral treatment device and a method of using the same. The oral treatment device includes an intraoral mouthpiece configured for placement into a mouth of a user. The intraoral mouthpiece includes an arcuate wall having a front surface and a bite platform extending from the front surface. Furthermore, there is an alignment feature located on the bite platform to facilitate consistent positioning of the intraoral mouthpiece within the user's mouth in a repeatable manner. The alignment feature may have a top surface that is inclined upwardly moving in a direction away from the front surface of the arcuate wall. The intraoral mouthpiece may also include a color measurement sensor for obtaining a color measurement of a tooth of the user.

In one aspect, the invention may be an oral treatment device comprising: an intraoral mouthpiece comprising: an arcuate wall comprising a concave front surface; a bite platform extending from the concave front surface of the arcuate wall; an alignment feature; and a color measurement sensor positioned along the arcuate wall, the color measurement sensor comprising a light emitter configured to emit light onto the tooth and a light receiver configured to receive reflected light that has reflected from the tooth to determine a color value for the tooth; and wherein the alignment feature is configured to ensure that each time the intraoral mouthpiece is positioned into a mouth of a user, a tooth of the user is located at a same distance from the color measurement sensor so that the reflected light is reflected from an identical location along the tooth when the color measurement sensor is activated.

The invention may be directed to a system for oral treatment which comprises the oral treatment device described in the above paragraph, and an electronic device comprising a software application that is in operable communication with the oral treatment device, wherein the software application is configured to control activation of the color measurement sensor, the plurality of first electromagnetic radiation emitting elements, and the plurality of second electromagnetic radiation emitting elements.

In another aspect, the invention may be an oral treatment device comprising: an intraoral mouthpiece comprising: an arcuate wall comprising a front surface; a bite platform extending from the front surface of the arcuate wall; an alignment feature located on or adjacent to the bite platform, the alignment feature comprising a top surface that is inclined upwardly moving in a direction away from the front surface of the arcuate wall; and a color measurement sensor aligned with the alignment feature and configured to obtain a color measurement of a tooth that is located along the alignment feature.

In yet another aspect, the invention may be an oral treatment device comprising: an intraoral mouthpiece comprising: an arcuate wall comprising a front surface; a bite platform extending from the front surface of the arcuate wall; a lamp positioned adjacent to the arcuate wall and configured to emit electromagnetic radiation onto oral surfaces when the intraoral mouthpiece is positioned within a mouth of a user and activated, the lamp comprising: a top edge and a bottom edge; a plurality of first electromagnetic radiation emitting elements that emit a violet light when activated; and a plurality of second electromagnetic radiation emitting elements that emit a red light when activated; and wherein the plurality of second electromagnetic radiation emitting elements comprises a first row positioned adjacent to the top edge of the lamp to emit the red light onto the user's gums when activated, and wherein each of the plurality of first electromagnetic radiation emitting elements is located between the first row of the plurality of second electromagnetic radiation emitting elements and the bottom edge of the lamp to emit the violet light onto the user's teeth when activated.

In still another aspect, the invention may be a method of obtaining a color measurement of a tooth at a consistent location on the tooth, the method comprising: inserting an intraoral mouthpiece into a mouth of a user, the intraoral mouthpiece comprising an alignment feature that ensures that a central incisor of the user is positioned at the same location relative to a color measurement sensor of the intraoral mouthpiece each time the intraoral mouthpiece is inserted into the mouth of the user; flashing a light onto the central incisor of the user via a light emitter of the color measurement sensor of the intraoral mouthpiece; receiving, by a light receiver of the color measurement sensor of the intraoral mouthpiece, reflected light that has reflected from a measurement location of the central incisor of the user; and determining a color measurement value based on the reflected light received by the light receiver.

In a further aspect, the invention may be a method of obtaining a color measurement of a tooth at a consistent location on the tooth, the method comprising: inserting an intraoral mouthpiece into a mouth of a user such that a central incisor of the user is positioned at the same location relative to a color measurement sensor of the intraoral mouthpiece each time the intraoral mouthpiece is inserted into the mouth of the user; flashing a light onto the central incisor of the user via a light emitter of the color measurement sensor of the intraoral mouthpiece; receiving, by a light receiver of the color measurement sensor of the intraoral mouthpiece, reflected light that has reflected from a measurement location of the central incisor of the user; determining a color measurement value based on the reflected light received by the light receiver; and wherein the measurement location of the central incisor is consistently the same location of the central incisor each time the intraoral mouthpiece is placed into the mouth of the user.

In another aspect, the invention may be an oral treatment device comprising: an intraoral mouthpiece comprising: an arcuate wall comprising a front surface; a bite platform extending from the front surface of the arcuate wall; a plurality of first electromagnetic radiation emitting elements that emit a first light having a first wavelength from the front surface of the arcuate wall when activated; and a plurality of second electromagnetic radiation emitting elements that emit a second light having a second wavelength from the front surface of the arcuate wall when activated; and wherein the plurality of second electromagnetic radiation emitting elements comprises a first row located adjacent to a top edge of the front surface of the arcuate wall and a second row located adjacent to a bottom edge of the front surface of the arcuate wall to emit the second light onto a user's gums when activated, and wherein each of the plurality of first electromagnetic radiation emitting elements is located along the arcuate wall at a position between the first and second rows of the plurality of second electromagnetic radiation emitting elements to emit the first light onto the user's teeth when activated.

In yet another aspect, the invention may be a tooth whitening method comprising: inserting an intraoral mouthpiece into a mouth of a user; activating a color measurement sensor of the intraoral mouthpiece to obtain a baseline color measurement of a specific tooth of the user; removing the intraoral mouthpiece from the mouth of the user; applying a tooth whitening composition onto a set of teeth of the user; reinserting the intraoral mouthpiece into the mouth of the user; activating a plurality of first electromagnetic radiation emitting elements to emit a first light having a first wavelength onto the teeth of the user for a first period of time; after expiration of the first period of time, removing the intraoral mouthpiece from the mouth of the user and leaving the tooth whitening composition onto the teeth for a second period of time; after expiration of the second period of time, removing the tooth whitening composition from the teeth of the user; and after removing the tooth whitening composition from the teeth of the user, reinserting the intraoral mouthpiece into the mouth of the user and activating a plurality of second electromagnetic radiation emitting elements to emit a second light having a second wavelength onto gums of the user for a third period of time.

In another aspect, the invention may be an oral care kit comprising an intraoral mouthpiece comprising a color measurement sensor and a plurality of first and second electromagnetic radiation emitting elements; a tooth whitening composition; and instructions for performing a tooth whitening method according using the intraoral mouthpiece and the tooth whitening composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
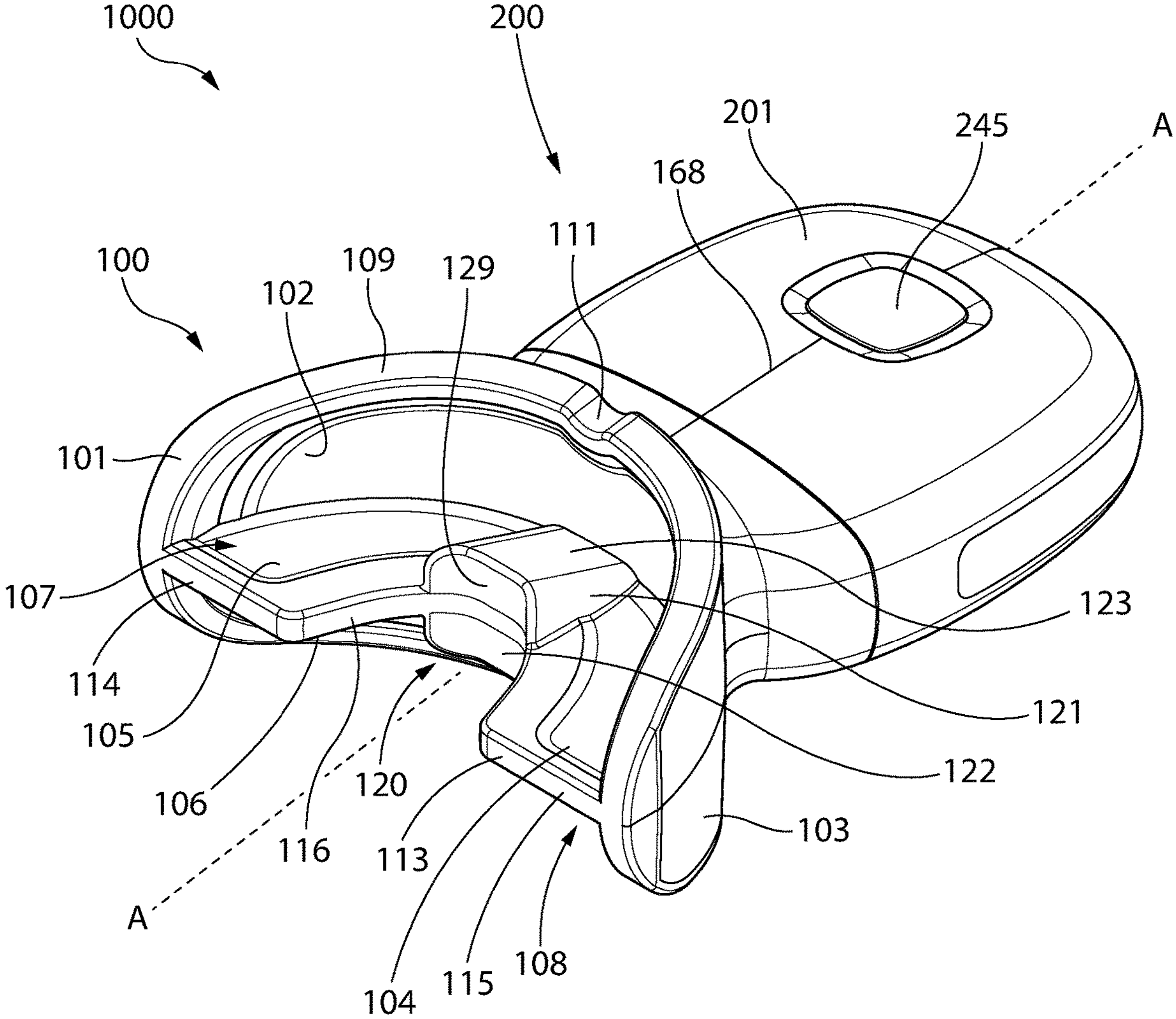
FIG. 1 is a front top perspective view of an oral treatment device in accordance with an embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Referring first to FIGS. 1-4 concurrently, an oral treatment device 1000 will be described in accordance with an embodiment of the present invention. The oral treatment device 1000 generally comprises an intraoral mouthpiece 100 and a handle 200. The intraoral mouthpiece 100 is configured for insertion into a user's mouth to perform a whitening treatment on the user's teeth and/or to obtain a color measurement for one or more of the user's teeth. The handle 200 comprises a housing 201 that is configured to contain certain electronic components of the oral treatment device 1000. The oral treatment device 1000 is configured so that the intraoral mouthpiece 100 is located within the user's mouth during use while the handle 200 is located external to the user's mouth during use.

The intraoral mouthpiece 100 comprises an arcuate wall 101 comprising a concave front surface 102 and a convex rear surface 103. The convex rear surface 103 of the arcuate wall 101 forms the convex rear surface of the intraoral mouthpiece 100. The handle 200 extends from the convex rear surface 103 of the arcuate wall 101/intraoral mouthpiece 100 and terminates at a distal end surface 230. The shape of the arcuate wall 101 generally corresponds to the overall shape of the front surfaces of the user's teeth. When the intraoral mouthpiece 100 is placed into the user's mouth, the arcuate wall 101 is positioned with the concave front surface 102 facing the outer surfaces of the user's teeth. Moreover, the user's lips may wrap over the top edge of the arcuate wall 101 and around a portion of the convex rear surface 103 of the arcuate wall 101 to hold the intraoral mouthpiece 100 in place within the user's mouth during use. The user may or may not grasp the handle 200 to further assist in holding the intraoral mouthpiece 100 in place within the mouth during use. During use of the intraoral mouthpiece 100, different types of electromagnetic radiation are emitted from the concave front surface 102 of the arcuate wall 101 onto teeth of a user that are placed adjacent thereto. However, before discussing the electromagnetic radiation and other functions of the oral treatment device 1000, the structure of the intraoral mouthpiece 100 will be described in greater detail.

Figure 3:
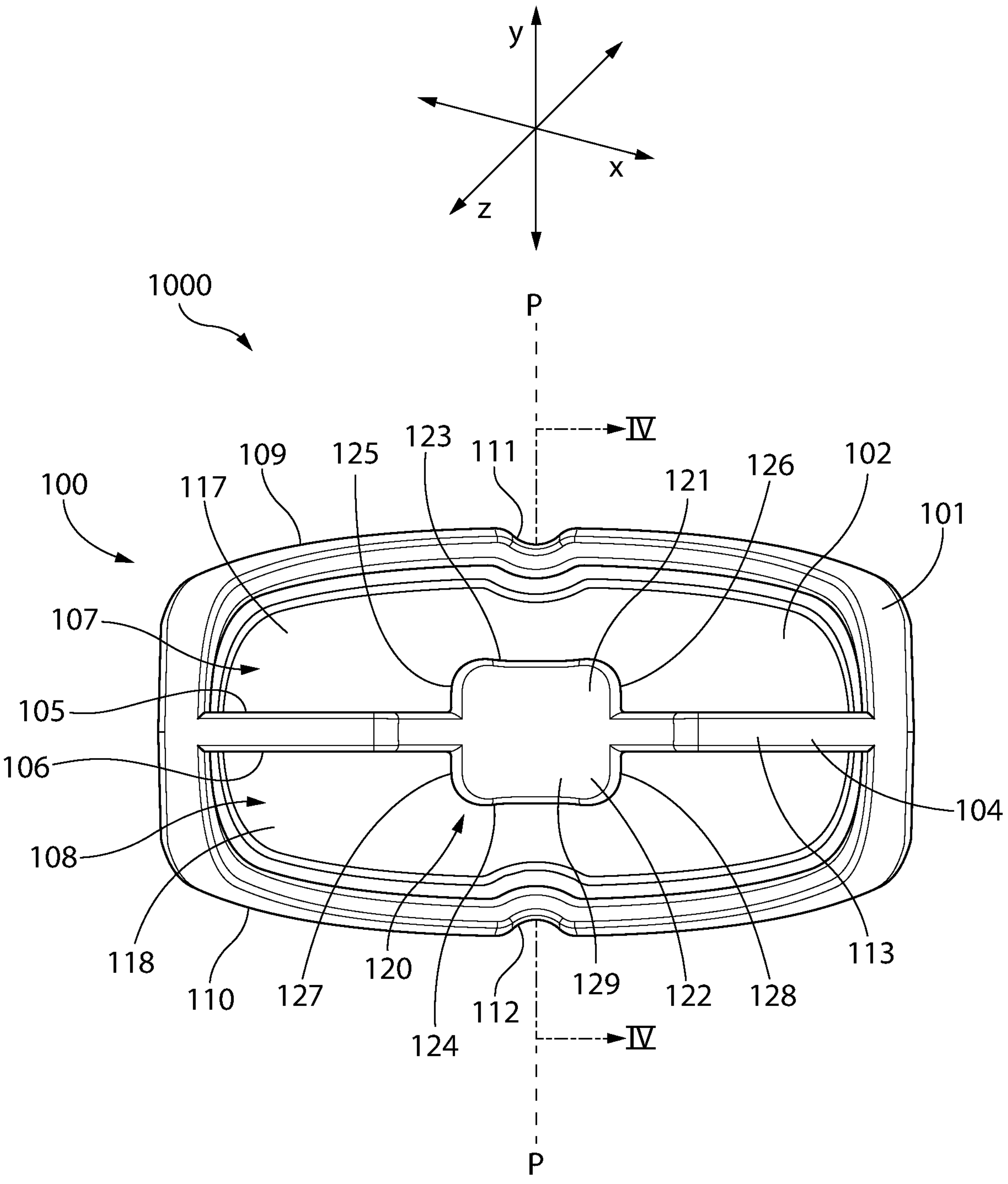
FIG. 3 is a front view of the oral treatment device of FIG. 1.

The arcuate wall 101 comprises a top end 109 and a bottom end 110. Furthermore, the arcuate wall 101 of the intraoral mouthpiece 100 is symmetric about a dental arch midline plane P-P. The dental arch midline plane P-P is a plane that is located centrally between the two side ends of the mouthpiece 100, intersects the top and bottom ends 109, 110 of the mouthpiece 100, and is perpendicular to an arcuate axis upon which the arcuate wall 101 extends. The arcuate wall 101 comprises a first notch 111 in the top end 109 and a second notch 112 in the bottom end 110. The first and second notches 111, 112 are aligned with each other along the arcuate axis, and are also aligned with the dental arch midline plane P-P. When a user inserts the intraoral mouthpiece 100 into his or her mouth, the user can shift the intraoral mouthpiece 100 side-to-side until the first and second notches 111, 112 are located centrally along the user's mouth or lips. Thus, the first and second notches 111, 112 may be used as a visual alignment feature to facilitate the user properly positioning the intraoral mouthpiece 100 in the mouth in the X-axis direction of a three dimensional Cartesian coordinate system as shown in FIG. 3. However, because the first and second notches 111, 112 are located within the user's mouth during use of the oral treatment device 1000, there may be a desire or need for additional visual alignment features on the handle 200, as described further below.

The intraoral mouthpiece 100 comprises a bite platform 104 that extends from the concave front surface 102 of the arcuate wall 101. The bite platform 104 extends horizontally outward from the concave front surface 102 of the arcuate wall 101 and divides the arcuate wall 101 into an upper portion 117 and a lower portion 118. When the intraoral mouthpiece 100 is positioned within the user's mouth, the bite platform 104 is intended to be located between the biting surfaces (occlusal or incisal surfaces) of the maxillary and mandibular teeth. That is, the bite platform 104 comprises an upper surface 105 and a lower surface 106. The upper surface 105 of the bite platform 104 and the concave front surface 102 of the arcuate wall 101 collectively define an upper channel 107. The lower surface 105 of the bite platform 104 and the concave front surface 102 of the arcuate wall 101 collectively define a lower channel 108. When the intraoral mouthpiece 100 is located within the user's mouth, the user's maxillary teeth are located within the upper channel 107 and the user's mandibular teeth are located within the lower channel 108, with the bite platform 104 being located between the user's maxillary and mandibular teeth.

In the exemplified embodiment, the upper surface 105 of the bite platform 104 and the lower surface 106 of the bite platform 104 are generally planar and parallel to one another. However, the invention is not to be so limited in all embodiments and the upper and lower surfaces 105, 106 of the bite platform 104 may take on other configurations in other embodiments. For example, the upper and/or lower surfaces 105, 106 of the bite platform 104 could be wavy or include pockets or recesses designed to receive the teeth of the user. The bite platform 104 extends from the concave inner surface 102 of the arcuate wall 101 to a distal edge 113. That is, the bite platform 104 terminates at a distal edge 113 that extends between the upper and lower surfaces 105, 106 of the bite platform 104. The distal edge 113 of the bite platform 104 comprises a first linear section 114 adjacent to a first side end of the arcuate wall 101, a second linear section 115 adjacent to a second side end of the arcuate wall 101, and an arcuate section 116 extending between the first and second linear sections 114, 115. The arcuate section 116 of the distal edge 113 of the bite platform 104 is concave in the exemplified embodiment. When the intraoral mouthpiece 100 is positioned within the user's mouth, the user's tongue may rest within the pocket formed between the first and second linear sections 114, 115 of the distal edge 113 of the bite platform 104.

In the exemplified embodiment, there is an alignment feature 120 located on, or along, the bite platform 104. In the exemplified embodiment, the alignment feature 120 is located on the bite platform 104. However, the invention is not to be so limited in all embodiments and the alignment feature may be located adjacent to or along the bite platform 104 without being located on or otherwise being coupled directly to the bite platform 104. For example, the alignment feature 120 may extend from the concave inner surface 102 of the arcuate wall 101 while being elevated relative to the bite platform 104, or to portions of the bite platform 104 with which the alignment feature 120 is aligned.

The alignment feature 120 is configured to ensure that each time the intraoral mouthpiece 100 is positioned into the mouth of the user, a particular tooth (e.g., one of the central incisors of the maxillary teeth) is located at the same position within the intraoral mouthpiece 100, or more specifically relative to a color measurement sensor of the intraoral mouthpiece 100 (the color measurement sensor will be described in greater detail below). In one embodiment, the alignment feature 120 is configured to ensure that the particular tooth is spaced the same distance from the concave front surface 102 of the arcuate wall 101 (and also from the color measurement sensor) each time the intraoral mouthpiece 100 is placed into the user's mouth. Stated another way, the alignment feature 120 is configured to ensure that the mouthpiece 100 is consistently positioned in the user's mouth in the direction of the Z-axis of the three-dimensional Cartesian coordinate system as shown in FIG. 3. It should be noted that the Z-distance (i.e., the distance between the concave inner surface 102 of the arcuate wall 101 and the front surface of the tooth being measured by the color measurement sensor) should be kept consistent for each particular user. The Z-distance is driven, in part, by the alignment feature 120 and comfort to a particular user, and may therefore differ from user to user. Thus, the Z-distance may be different from user to user, but should be consistent for a particular user each time the user inserts the intraoral mouthpiece 100 into his or her mouth in order to ensure consistent color measurements are taken from the same spot on the same tooth, as described herein in some detail.

In accordance with the exemplified embodiment, it is important to ensure that the particular tooth who's color is to be measured by the color measurement sensor is consistently positioned at the same relative location along the intraoral mouthpiece 100 (and relative to the color measurement sensor). This is because the oral treatment device 1000 is configured to obtain a color measurement for the particular tooth using the color measurement sensor (which will be described below with reference to FIGS. 6 and 8). Thus, by ensuring that the particular tooth is consistently positioned at the same location relative to the color measurement sensor, the color measurement can be taken from the same spot on the particular tooth in each instance. Stated another way, the color measurement can be taken from an identical location along the selected tooth. The term identical location may include a tolerance of up to 1 mm in any direction. If the particular tooth could be located at different positions relative to the color measurement sensor upon each insertion of the intraoral mouthpiece 100 into the user's mouth, then the color measurement could be taken at different spots along the particular tooth. This can result in an inadequate indication being provided to the user regarding a change in the color measurement over time. Specifically, the particular tooth being measured may have different colors or different shades of color at different positions therealong. Thus, if the color measurement is taken at a first spot along the tooth on day one and then at a second different spot along the tooth on day two, the indication provided to the user regarding any change in color between days one and two as a result of a whitening treatment being performed may not be accurate. The present invention helps to ensure that the color measurement is taken from the same spot (or identical location, within the tolerance noted) on the same tooth each time the intraoral mouthpiece 100 is positioned into the mouth of the user and used to take a color measurement.

As noted above, in the exemplified embodiment the particular tooth is one of the central incisors of the user's maxillary teeth. The reason that this particular tooth is chosen is that most people have central incisors, and the central incisors are the teeth that are most frequently visible to others. However, while the central incisors are indicated as the teeth intended to be measured for color using the oral treatment device 1000 in accordance with the exemplified embodiment of the present invention, the invention is not to be so limited in all embodiments. The particular tooth could theoretically be any tooth in the user's mouth, and the intraoral mouthpiece 100, and more particularly the alignment feature 120 thereof, is configured to ensure that whatever tooth is being measured, it is consistently located at the same position relative to the color measurement sensor each time the intraoral mouthpiece 100 is placed into the user's mouth.

Moreover, while the invention is described herein wherein there is only one color measurement sensor, the invention is not to be so limited in all embodiments. Thus, in other embodiments, the oral treatment device 1000 may comprise multiple color measurement sensors, each positioned and configured to take a color measurement for a different specific tooth in the mouth. This can be beneficial for several reasons. First, the oral treatment device 1000 or an electronic device operably coupled thereto (as described herein) may have an algorithm that can determine a whiteness score based on the color measurement taken from multiple teeth. Second, some people may be missing certain teeth or may have veneers that do not whiten or change color. By having multiple color measurement sensors, there is a greater likelihood that at least one of the color measurement sensors will be aligned with one of the user's original teeth, rather than a spot where a tooth is missing or a veneer or other replacement tooth is located. In some embodiments, a user may be able to select which color measurement sensor to activate so that while the oral treatment device 1000 may include multiple color measurement sensors, only one is activated during a treatment protocol (which occurs over the course of many days or weeks) to ensure results are taken from the same singular tooth during the course of the treatment. This will enable a user to determine a color measurement sensor to use based on ensuring that it is aligned with a real tooth of the user rather than with a missing tooth location or veneer or the like. The color measurement sensors could be aligned only with the top teeth, with the top teeth and the bottom teeth, only with the bottom teeth, or the like.

In the exemplified embodiment, the alignment feature 120 is aligned with the dental arch midline plane P-P. More specifically, in the exemplified embodiment the alignment feature 120 is symmetric about the dental arch midline plane P-P. However, the invention is not to be so limited in all embodiments and in other embodiments the alignment feature 120 may be positioned at other locations along the bite platform 104. For example, in one embodiment there may be two alignment features located on opposing ends of the bite platform 104 where the user's molars would be located when the intraoral mouthpiece 100 is positioned in the user's mouth.

In the exemplified embodiment, the alignment feature 120 is a wedge-shaped element that protrudes from both of the upper and lower surfaces 105, 106 of the bite platform 104. Thus, the alignment feature 120 comprises a first portion 121 that protrudes into the upper channel 107 and is aligned with the upper portion 117 of the arcuate wall 101 and a second portion 122 that protrudes into the lower channel 108 and is aligned with the lower portion 118 of the arcuate wall 101. The first portion 121 of the alignment feature 120 extends upwardly from the upper surface 105 of the bite platform 104 and the second portion 122 of the alignment feature 120 extends downwardly from the lower surface 106 of the bite platform 104. However, the invention is not to be so limited in all embodiments. In some embodiments, the alignment feature 120 may comprise only the first portion 121 and not the second portion 122, or vice versa.

The alignment feature 120 extends from the upper surface 105 of the bite platform 104 to a top surface 123. The top surface 123 of the alignment feature 120 is sloped or inclined upwardly moving in a direction away from the concave inner surface 102 of the arcuate wall 101 towards the distal end 113 of the bite platform 104. Stated another way, the top surface 123 is inclined upwardly with increasing distance from the arcuate wall 101. In the exemplified embodiment, the top surface 123 is planar and extends along an axis that is acute to the upper surface 105 of the bite platform 104. However, the top surface 123 need not be planar in all embodiments, and could instead have a wavy or undulating configuration without affecting its function. The top surface 123 is elevated relative to the upper surface 105 of the bite platform 104 along its entire length, including at its lowest point where the top surface 123 of the alignment feature 120 intersects or meets the concave inner surface 102 of the arcuate wall 101. In other embodiments, the end of the alignment feature 120 that is adjacent to the arcuate wall 101 may be flush with the upper surface 105 of the bite platform 104. The height of the first portion 121 of the alignment feature 120 measured from the upper surface 105 of the bite platform 104 to the top surface 123 of the alignment feature 120 increases continuously moving from the arcuate wall 101 to the distal end 113 of the bite platform 104.

The alignment feature 120 comprises a first upper side surface 125 that extends from the top surface 123 of the alignment feature 120 to the upper surface 105 of the bite platform 104 and a second upper side surface 126 that extends from the top surface 123 of the alignment feature 120 to the upper surface 105 to the bite platform 104. In the exemplified embodiment, the alignment feature 120 comprises a rounded corner where the top surface 123 meets each of the first and second upper side surfaces 125, 126. In other embodiments, the corner could be made sharp.

The alignment feature 120 extends from the lower surface 160 of the bite platform 104 to a bottom surface 124. The bottom surface 124 of the alignment feature 120 is sloped or inclined downwardly moving in the direction away from the concave inner surface 102 of the arcuate wall 101 towards the distal end 113 of the bite platform 104. Stated another way, the bottom surface 124 is inclined downwardly with increasing distance from the arcuate wall 101. In the exemplified embodiment, the bottom surface 124 is planar and extends along an axis that is acute to the lower surface 106 of the bite platform 104. Of course, the bottom surface 124 could be undulating or wavy or otherwise non-planar in other embodiments without affecting the function. The bottom surface 124 is elevated relative to the lower surface 106 of the bite platform 104 along its entire length, including at its lowest point where the bottom surface 124 of the alignment feature 120 intersects or meets the concave inner surface 102 of the arcuate wall 101. In other embodiments, the end of the alignment feature 120 that is adjacent to the arcuate wall 101 may be flush with the lower surface 106 of the bite platform 104. The height of the second portion 122 of the alignment feature 120 measured from the lower surface 106 of the bite platform 104 to the bottom surface 124 of the alignment feature 120 increases continuously moving from the arcuate wall 101 to the distal end 113 of the bite platform 104.

The top and bottom surfaces 123, 124 of the alignment feature 120 are sloped or inclined so as to diverge as they extend further from the concave inner surface 102 of the arcuate wall 101. Thus, due to the angle at which the top and bottom surfaces 123, 124 of the alignment feature 120 are oriented, the thickness of the alignment feature 120 increases moving in the direction away from the concave inner surface 102 of the arcuate wall 101.

It should be appreciated that the terms top and bottom with regard to the top and bottom surfaces 123, 124 are not intended to be limiting of the invention in all embodiments. For example, in some embodiments the intraoral mouthpiece 100 may be able to be flipped/rotated 180°, such that the top surface 123 is located at the bottom and the bottom surface 124 is located at the top. Thus, the terms top surface 123 and bottom surface 124 would be interchangeable, and may simply refer to a first surface and a second surface in some embodiments.

The alignment feature 120 comprises a first lower side surface 127 that extends from the bottom surface 124 of the alignment feature 120 to the lower surface 106 of the bite platform 104 and a second lower side surface 128 that extends from the bottom surface 124 of the alignment feature 120 to the lower surface 106 of the bite platform 104. In the exemplified embodiment, the alignment feature 120 comprises a rounded corner where the bottom surface 124 meets each of the first and second lower side surfaces 127, 128. In other embodiments the corner could be sharp and not rounded.

The alignment feature 120 terminates in a distal surface 129. In the exemplified embodiment, the distal surface 129 of the alignment feature 120 is flush with the distal edge 113 of the bite platform 104 along the arcuate section 116 of the distal edge 113 of the bite platform 104. Moreover, because the distal surface 129 of the alignment feature 120 is located along the arcuate section 116 of the distal edge 113 of the bite platform 104, the distal surface 129 of the alignment feature 120 is also arcuate, and more specifically concave. However, this is not required in all embodiments and the distal surface 129 of the alignment feature 120 may be planar or the like in other embodiments.

As stated above, the alignment feature 120 has an overall wedge-like shape. Due to the sloping top and bottom surfaces 123, 124 of the alignment feature, 120, when the user places the intraoral mouthpiece 100 into his or her mouth, the user will be guided to pull the intraoral mouthpiece 100 a particular distance into the mouth to achieve a desired level of comfort. In particular, the user's central incisors will likely rest in contact with the top and bottom surfaces 123, 124 of the alignment feature 120 when the intraoral mouthpiece 100 is located in the mouth. If the user's central incisors are located near the distal surface 129 of the alignment feature 120 this will require the user to maintain the mouth in a slightly open position. Thus, the user will be guided and encouraged to insert the intraoral mouthpiece 100 further into the mouth until the central incisors are located in close proximity to the concave inner surface 102 of the arcuate wall 101. The alignment feature 120 has been found to result in user's having much greater consistency with the placement of the intraoral mouthpiece 100 in the mouth as compared to intraoral mouthpieces that do not include such an alignment feature. As noted above, the distance between the specific tooth that is to be measured and the color measurement sensor will dictate which spot on the tooth that the color measurement is measured at. Thus, maintaining a consistent distance between the specific tooth that is to be measured and the color measurement sensor (and the inner surface 102 of the arcuate wall 101) each time that the mouthpiece 100 is inserted into the mouth is an important function of the alignment feature 120 described herein.

In the exemplified embodiment, the alignment feature 120 is located entirely in alignment with the arcuate section 116 of the distal edge 113 of the bite platform 104. Thus, the alignment feature 120 is centrally located along the bite platform 104. In the exemplified embodiment, the top and bottom surface 123, 124 of the alignment feature 120 are sloped moving in the direction between the concave inner surface 102 of the arcuate wall 101 and the distal edge 113 of the bite platform 104. As mentioned above, the alignment feature 120 could be located at other positions along the bite platform 104. For example, in one embodiment there could be two of the alignment features 120, one located on either of the opposing ends of the bite platform 104. In such an embodiment, the slope of the top and bottom surfaces 123, 124 of the alignment feature 104 would be in a direction towards the first and second linear sections 114, 115 of the distal edge 113 of the bite platform 104. Stated another way, the slope or incline of the top and bottom surfaces 123, 124 should be in the direction of the translational movement of the intraoral mouthpiece 100 when it is being inserted into the mouth. As such, as the user's teeth are moving along the bite platform 104 during the insertion, the maxillary and mandibular teeth will be able to come closer together as the intraoral device 100 is inserted deeper into the mouth. In the exemplified embodiment the handle 200 extends from the intraoral mouthpiece 100 along an axis A-A, and the top and bottom surfaces 123, 124 of the alignment feature 120 are sloped in the direction of (or in a direction parallel to) the axis A-A. The alignment feature 120 could also be located at other positions along the bite platform 104, such as between the ends and the center positions described above.

Figure 1A:
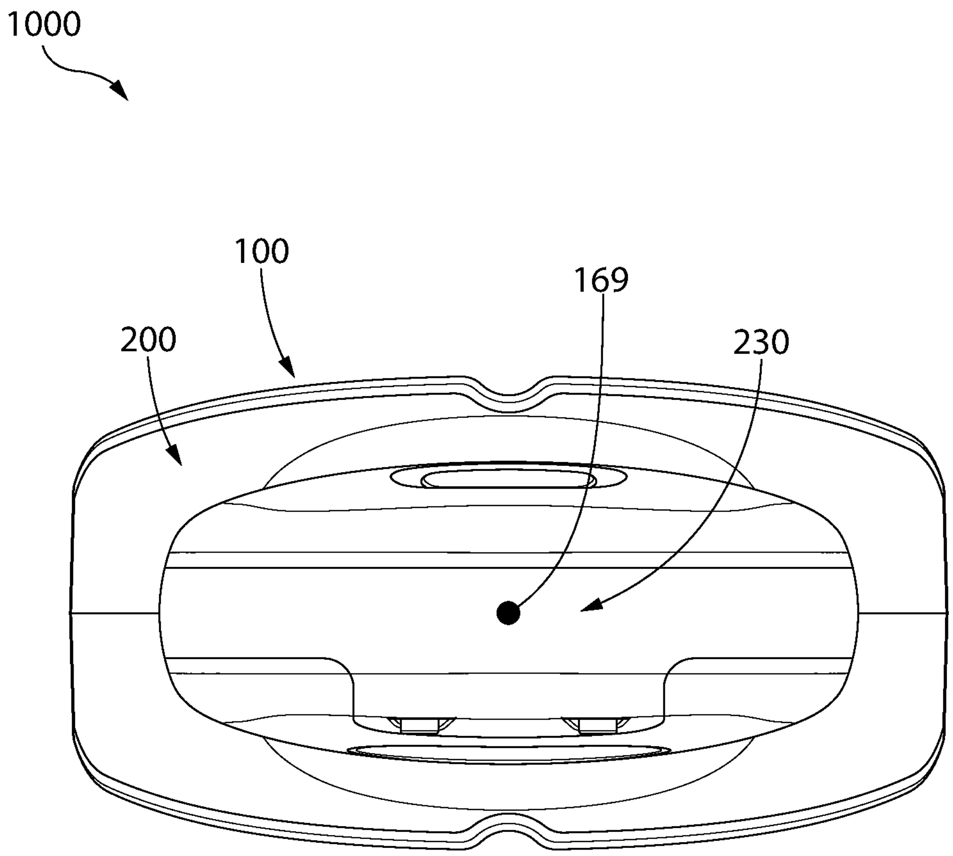
FIG. 1A is a rear view of the oral treatment device of FIG. 1.
Figure 2:
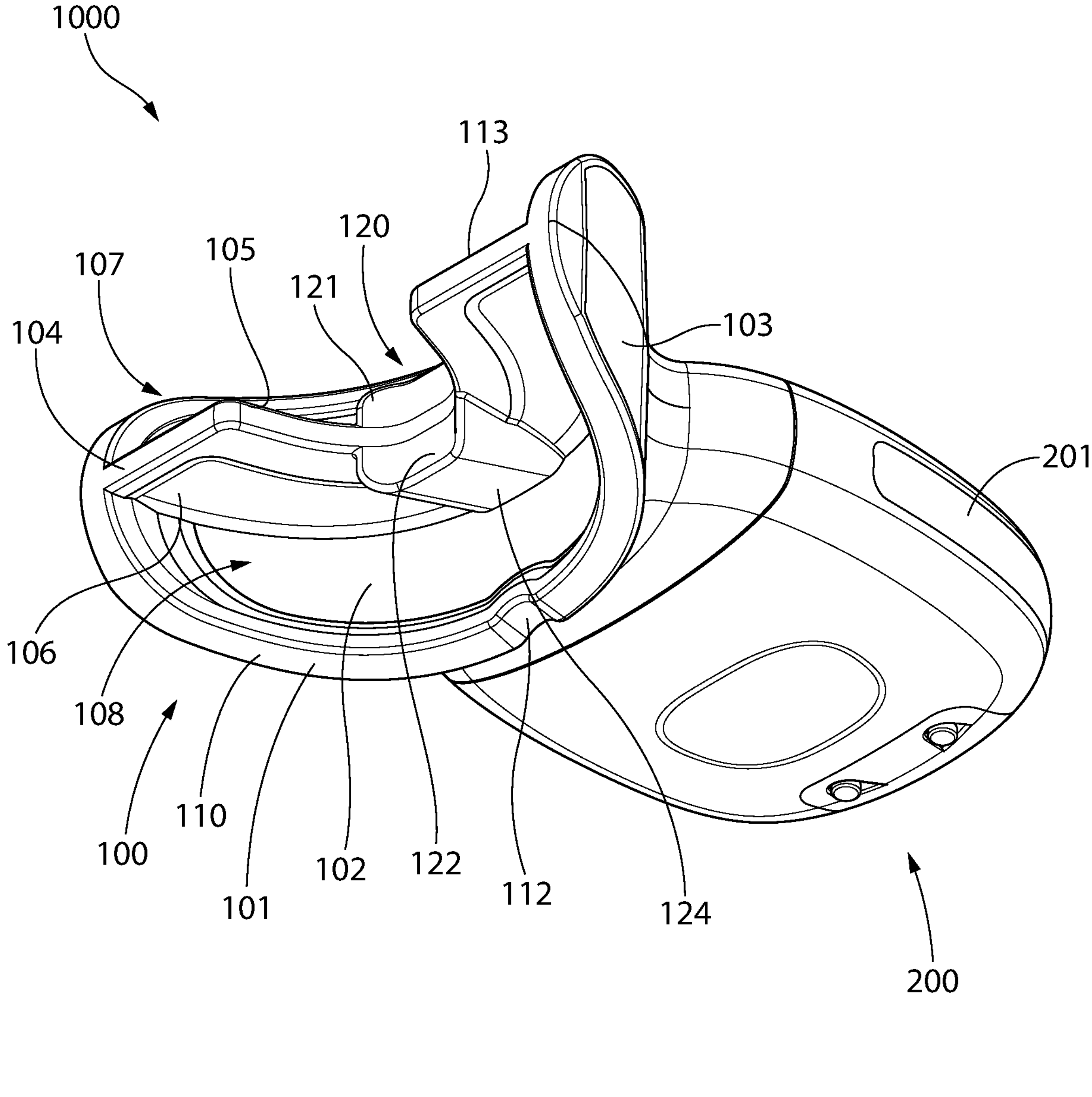
FIG. 2 is a front bottom perspective view of the oral treatment device of FIG. 1.

As noted above, the handle 200 of the oral treatment device 1000 comprises a housing 201 that houses various electronic components of the oral treatment device 1000. Thus, the housing 201 defines an interior cavity 202 within which the electronic components may be disposed. Furthermore, the housing 201 of the handle 200 has an outer surface, which may include a visual alignment feature 168. The visual alignment feature 168 is aligned with the notch 111 and is intended to assist a user in properly positioning the intraoral mouthpiece 100 into the mouth in the X direction of the Cartesian coordinate system shown in FIG. 3. As mentioned above, the intraoral mouthpiece 100 which includes the notch 111 is located in the mouth during use, and thus the notch 111 may not be overly helpful for purposes of alignment. However, if a user is standing in front of a mirror, the housing 201 and the handle 200 are located outside of the mouth and can help with the alignment in the X direction. The visual alignment feature 168 is located centrally along the oral treatment device 1000 to help a user center the oral treatment device 1000 in the mouth in the X direction. The visual alignment feature 168 may be a line as shown, which may be drawn or painted onto the housing 201, or the visual alignment feature 168 may be an indentation or the like formed into the housing 201 which may be formed during the manufacturing/molding process. Moreover, as shown in FIG. 1A, the housing 201 may terminate at a distal end surface 230, and there may be an alignment indicium 169 located centrally along the distal end surface 230. This may be helpful since the distal end surface 230 will be visible to the user, and thus the user can centrally align the alignment indicium 169 along the user's face in the X direction. In the exemplified embodiment, the alignment indicium is a dot, but it may be an "X" or a star or a dash or any other indicium that may assist a user in properly centering the intraoral mouthpiece 100 within the mouth in the X direction.

The housing 201 of the handle 200 houses a control circuit 250 of the oral treatment device 1000. The housing 201 may also house a power source 240 within the interior cavity 202. The handle 200 also comprises an actuator 245 (i.e., a power button) for activating the control circuit 250 for operation of the oral treatment device 1000. The control circuit 250 may also comprise a communication component, such as a Bluetooth module, a Wi-Fi module, or the like, to enable electronic/wireless communication between the oral treatment device 1000 and an external electronic device such 900 as a smart phone (see FIG. 9).

Figure 9:
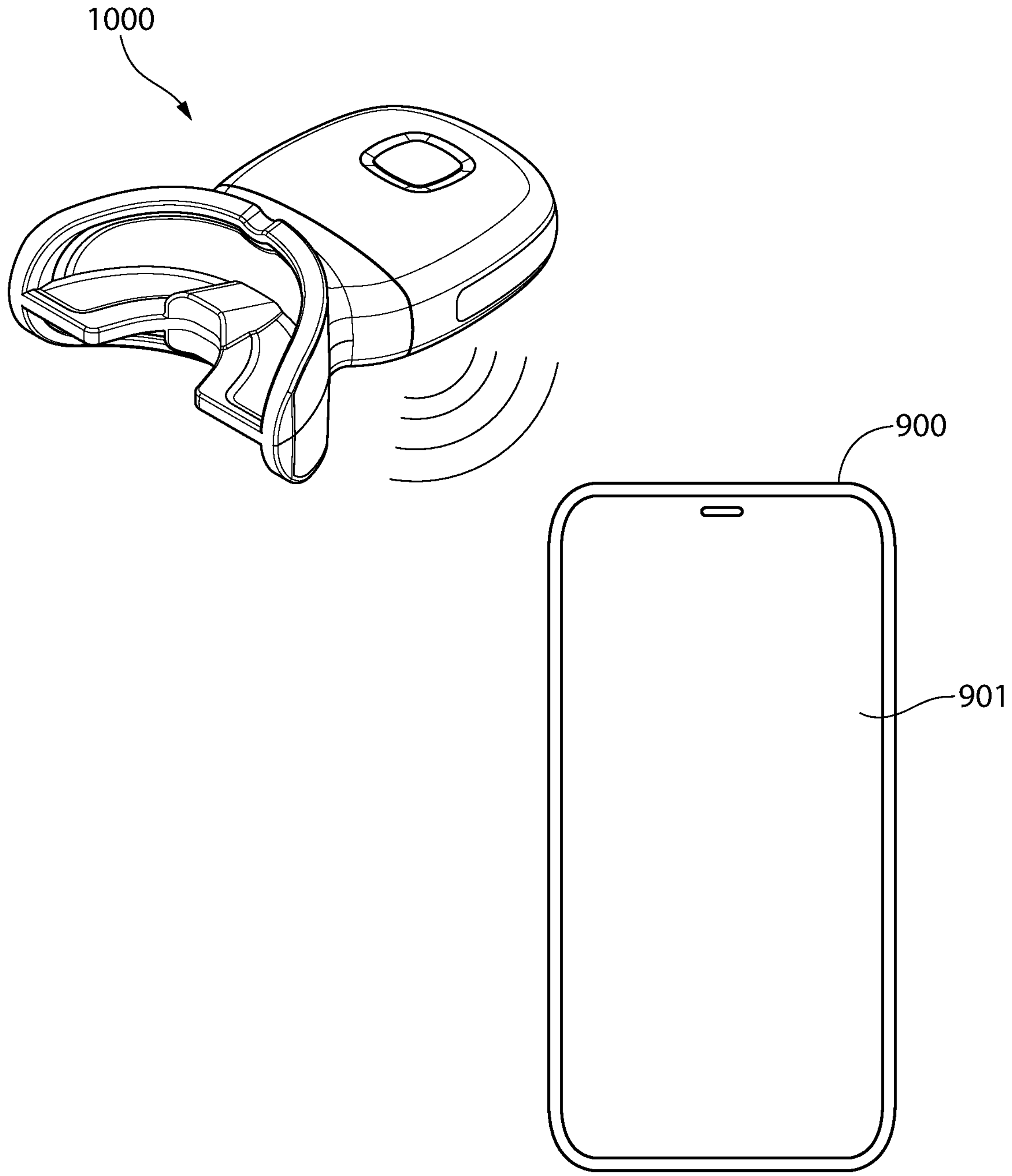
FIG. 9 is a schematic illustration of the oral treatment device of FIG. 1 in operable communication with an electronic device.

In the exemplified embodiment, actuation of the actuator 245 will power the oral treatment device 1000 on so that the oral treatment device 1000 may become operably coupled to the external electronic device 900 (see FIG. 9). The oral treatment device 1000 may become automatically wirelessly coupled to the electronic device 900 upon being powered on in some embodiments, although in other embodiments the user may be required to interact with one or both of the oral treatment device 1000 and the electronic device 900 to achieve the operable wireless coupling therebetween. In some embodiments, actuation of the actuator 245 may be used to control transmission of power from the power source 240 to an electromagnetic radiation source (described below) so that the electromagnetic radiation source can emit the electromagnetic radiation onto the user's teeth. However, in other embodiments the electronic device 900 shown in FIG. 9 may be used for activating the electromagnetic radiation source, and the power button or actuator 245 may simply power the device on to allow it to operably/wirelessly couple to the electronic device 900 for transmission of signals and/or data therebetween. As will be discussed below, it may be undesirable for a user to be able to activate the color measurement sensor with the actuator 245 because pressing the actuator 245 could change the alignment of the color measurement sensor with the tooth to be measured. Thus, as discussed herein, in preferred embodiments the user will use the electronic device 900 which is separate and distinct from the oral treatment device 1000 for purposes of activating the color measurement sensor, and possibly also for activating the various electromagnetic radiation emitting elements and other features of the oral treatment device 1000.

The oral treatment device 1000 may power off automatically after a predetermined period of time, and/or the oral treatment device 1000 may power off upon a second actuation of the actuator 245 or upon a second type of actuation of the actuator 245 (such as holding in the actuator 245 for five seconds, or pressing the actuator 245 twice in quick succession). In the exemplified embodiment, the actuator 245 is a depressible button, but the invention is not to be so limited and other types of actuators may be used. Specifically, the actuator 245 can be any type of device that upon actuation powers on and/or off one or more of the electrical components stored within the housing 201. For example, the actuator 245 can be a slide switch, a touch pad, a knob, a capacitive sensor, or any other component that upon actuation causes the oral treatment device 1000 to function as described herein. The actuator 245 may be operably coupled to a processor so that upon depressing or otherwise actuating the actuator 245, the processor initiates operation of the oral treatment device 1000 or initiates an attempt to wirelessly connect to another device, such as the electronic device 900 of FIG. 9.

Figure 4:
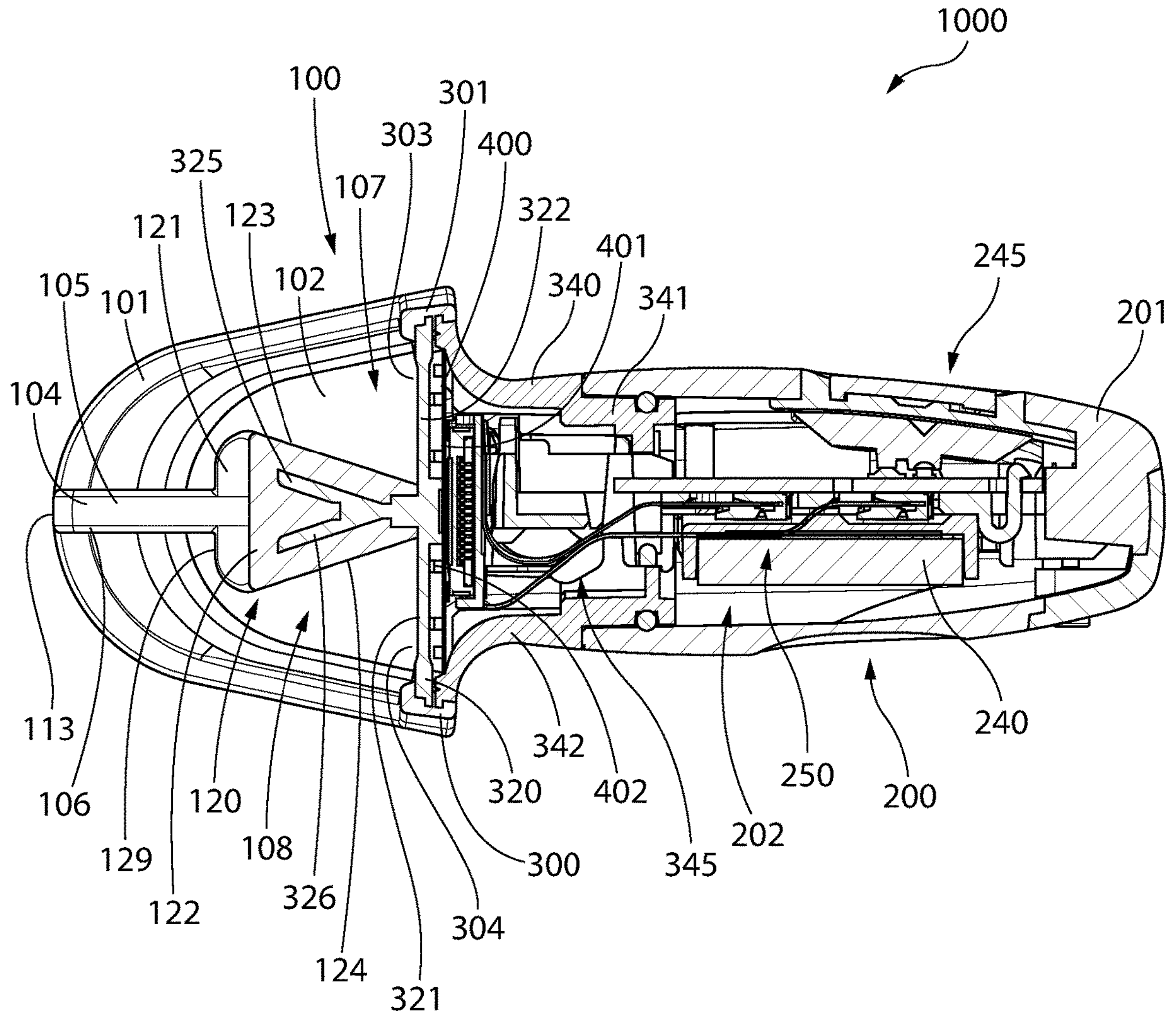
FIG. 4 is a cross-sectional view taken along line IV-IV of FIG. 3.
Figure 5:
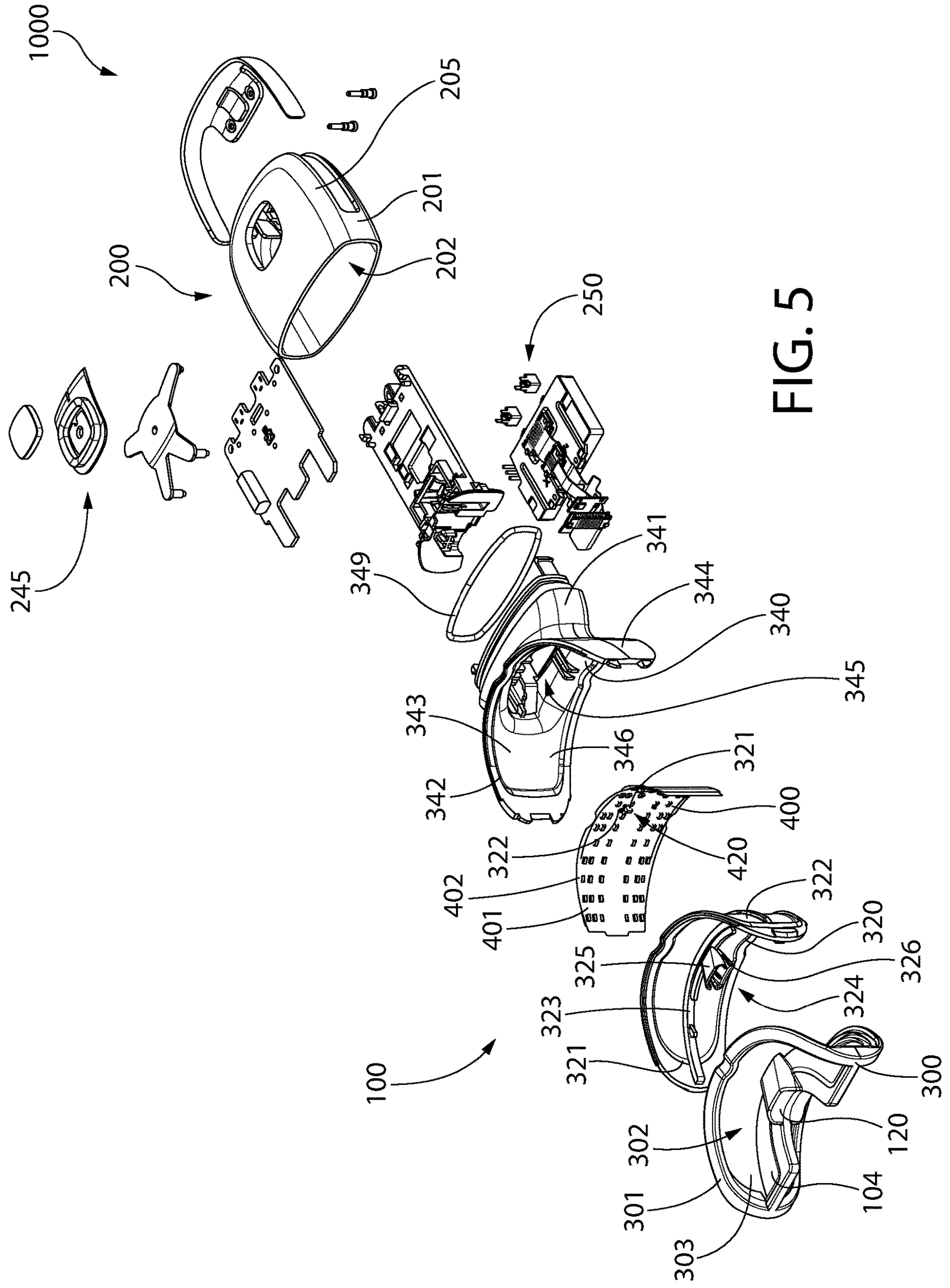
FIG. 5 is an exploded view of the oral treatment device of FIG. 1.

Referring to FIGS. 4 and 5, the oral treatment device 1000 and its constituent parts will be further described. While the oral treatment device 1000 was described above in its assembled state, the oral treatment device 1000 may be formed from several parts or components which are coupled together to form the final assembled product. In the exemplified embodiment, the oral treatment device 1000 comprises a guard component 300, a lens plate 320, a lamp 400, a lamp support structure 340, the control circuit 250, the actuator 245, and the handle 200.

The guard component 300 is the front-most part of the oral treatment device 1000 which abuts against the user's oral surfaces when the intraoral mouthpiece 100 is placed within the mouth. The guard component 300 comprises the bite platform 104, the alignment feature 120, and a frame portion 301. The guard component 300 may be formed of a resilient material such as a thermoplastic elastomer or other elastomeric material. Suitable elastomeric materials include, without limitation, thermoplastic elastomers, rubbers, silicones, or other biocompatible resilient materials suitable for uses in an oral hygiene apparatus including thermoset elastomers or the like. The reason for forming the guard component 300 out of an elastomeric material is that the guard component 300 is the main component that directly contacts the user's oral cavity surfaces during use of the oral treatment device 1000. Thus, forming the guard component 300 out of an elastomeric material enhances comfort to the user. The guard component 300 may be injection molded onto the lamp support structure 340 after the lamp 400 and the lens plate 320 are coupled to the lamp support structure 340 to complete the assembly of the intraoral mouthpiece 100. Alternatively, the guard component 300 could be formed separately from the lamp support structure 340 and merely coupled thereto using mechanical interfaces/mating between the components.

The frame portion 301 defines a window 302 that is divided by the bite platform 104 into an upper window 303 and a lower window 304. The frame portion 301 forms an enclosed geometric structure having an arcuate shape that appears rectangular when viewed from the front. The upper and lower windows 303, 304 are openings through which the lens plate 320 is exposed in the assembled intraoral mouthpiece 100. Thus, electromagnetic radiation emitted by the lamp 400 can pass through the lens plate 320 and through the upper and lower windows 303, 304 to reach a user's teeth and other oral surfaces as desired.

The lens plate 320 is positioned between the lamp 400 and the rear surface of the guard component 300. The lens plate 320 comprises a front surface (or inner surface) 321 that faces the rear surface of the guard component 300 and a rear surface (or outer surface) 322 opposite the front surface 321. The front or inner surface 321 is arcuate, and more specifically concave, and forms the concave front surface 102 of the arcuate wall 101 in the assembled intraoral mouthpiece 100. Because the lens plate 320 covers the lamp 400, the lens plate 320 is formed of a light transmissive material so that the light generated by light emitters of the lamp 400 can pass through the lens plate 320. Thus, in some embodiments the lens plate 320 may be formed of a transparent material. The lens plate 320 may also be formed of a translucent material. In some embodiments, the lens plate 320 may have a colored tint, while still being light transmissive so that light emitted by the lamp 400 can pass therethrough. In one particular embodiment, the lens plate 320 may be formed of a transparent biocompatible material. The lens plate 320 may be formed of a copolyester. In some embodiments the copolyester is Eastar™ BR003, although the invention is not to be so limited in all embodiments and the lens plate 320 may be formed of a number of different materials so long as it enables the light emitted by the lamp 400 to pass therethrough as described herein. One benefit of Eastar™ BR003 is that it contains a mold release additive and is nearly water-clear.

The lens plate 320 comprises a ridge 323 extending from the front surface 321 along a midline of the lens plate 320 halfway between top and bottom edges of the lens plate 320. When the intraoral mouthpiece 100 is assembled, the ridge 323 is embedded within the bite platform 104 of the guard component 300, which helps to facilitate a secure coupling between the lens plate 320 and the guard component 300. The lens plate 320 also comprises a protuberance 324 that protrudes either from the front surface 321 of the lens plate 320 or from the distal end of the ridge 323. The protuberance 324 comprises an upper portion 325 that is inclined upwardly in a direction away from the front surface 321 and a lower portion 326 that is inclined downwardly in a direction away from the front surface 321. When the intraoral mouthpiece 100 is assembled, the protuberance 324 is embedded within the alignment feature 120 of the guard component 300. Thus, the protuberance 324 provides some structural rigidity to the alignment feature 120 and helps to facilitate a secure coupling between the guard component 300 and the lens plate 320. However, the protuberance 324, and also the ridge 323, may be omitted in some embodiments.

In the exemplified embodiment, the lamp 400 is a singular structure that, when the oral treatment device 1000 is assembled, is located along the rear surface 322 of the lens plate 320 so as to emit electromagnetic radiation through the lens plate 320. The lamp 400 comprises a flexible sheet body 401, which is an elongated sheet that is sufficiently flexible such that it can be bent from a planar state into a contoured shape having a curvature that generally corresponds to the arch of a user's dentiture. In one embodiment, the flexible sheet body 401 is in a planar state when no bending force is applied thereto. In another embodiment, the flexible sheet body 401 is flat when no bending force is applied thereto, but the flexible sheet body 401 can be bent into the desired curvature such as for example to match the curvature of the lens plate 320.

The lamp 400 may comprise the flexible sheet 401 with a plurality of electromagnetic radiation emitting elements 402 and a color measurement sensor 420 located thereon. The electromagnetic radiation emitting elements 402 may be any type of device that is capable of generating and/or emitting light when coupled to a power source and activated. In one particular embodiment, the electromagnetic radiation emitting elements 402 may comprise light emitting diodes (LEDs), including printed LEDs. In other embodiments, the electromagnetic radiation emitting elements 402 may be any type of light source, particularly solid state light sources, which may include LEDs, OLEDs, HBLEDs, electroluminescent elements, or the like. In certain other embodiments, the plurality of electromagnetic radiation emitting elements 402 can be printed inorganic LEDs, micro conventional LEDs that are surface mounted to a flexible substrate/circuit, organic LEDs (OLEDs), or electroluminescence. In still other embodiments, the plurality of electromagnetic radiation emitting elements 402 can be any of the LEDs noted herein mounted to a rigid rather than a flexible substrate.

Additional details regarding the electromagnetic radiation emitting elements 402 will be provided below with reference to FIGS. 6-7C.

As noted above, in addition to the plurality of electromagnetic radiation emitting elements 402, the lamp 400 also comprises the color measurement sensor 420. The color measurement sensor 420 comprises a light emitter 421 and a light receiver 422. The color measurement sensor 420 will be described in greater detail below with particular reference to FIGS. 6 and 8. Moreover, while one color measurement sensor 420 is shown and described herein, as mentioned above the oral treatment device 1000 may comprise a plurality of color measurement sensors in other embodiments. In such an embodiment, each of the color measurement sensors may comprise a light emitter and a light receiver that receives reflected light from the light emitter. Each of the color measurement sensors may be aligned with a different one of the user's teeth for purposes of taking color measurements on the tooth with which it is aligned. In some embodiments all of the color measurement sensors may be activated at once. In other embodiments, a user may select which of the color measurement sensors to activate depending on the user's specific oral cavity, such as locations of missing teeth, veneers, other tooth implants, tooth visibility to others, or the like.

The lamp 400 may operate with a driving current that is less than or equal to 130 mA, although in some embodiments it may be between 75 mA and 105 mA. The lamp 400 may have an emittance at 90 mA that is greater than 9.2 mW/cm2. The lamp 400 may be divided into a plurality of distinct regions of equal surface area. Regardless of the breakdown of the regions, the lamp 400 may have a uniformity that is greater than 75% among the distinct regions. The lamp 400 may have a surface operating temperature that is below 48° C. when driven in accordance with the parameters set forth herein for a time period of 10 minutes.

The lamp 400 is sandwiched between the lens plate 320 and the lamp support structure 340. The lamp support structure 340 comprises a first portion 341 of the housing 201 of the handle 200 and a curved support plate 342 that supports the lamp 400. The handle 200 is formed by attaching a second portion 205 of the housing 201 to the first portion 341 of the housing 201, which renders the handle 200 attached to the lamp support structure 340. A gasket 349 may be positioned around the first portion 341 of the housing 201 to prevent liquid ingress into the interior cavity 202 of the housing 201. The curved support plate 342 comprises a concave front surface 343 and a convex rear surface 344. The lamp support structure 340 comprises an opening 345 that extends all the way through from the concave front surface 343 to the back end of the first portion 341 of the housing 201. In the assembled oral treatment device 1000, portions of the control circuit 250 may extend through the first portion 341 of the housing 201 and into the opening 345. For example, wires may extend from the power source and/or a processor or the like to the lamp 400 in order to provide an electrical coupling therebetween so that the lamp 400 may be powered when the oral treatment device 1000 is activated.

The lamp 400 is attached to the lamp support structure 340 along the concave front surface 343 of the curved support plate 342. In the exemplified embodiment, the concave front surface 343 comprises a recessed portion 346, and the lamp 400 nests within the recessed portion 346. This ensures that there is sufficient space for the lamp 400 and the electromagnetic radiation emitting elements 402 which protrude therefrom to fit between the curved support plate 342 of the lamp support structure 340 and the rear surface 322 of the lens plate 320.

Additional details about the various components of the oral treatment device 1000, their relationship to one another, and their functionality may be set forth in one or both of U.S. Pat. Nos. 11,040,218 and 10,369,375, the entireties of which are incorporated herein by reference.

Figure 6:
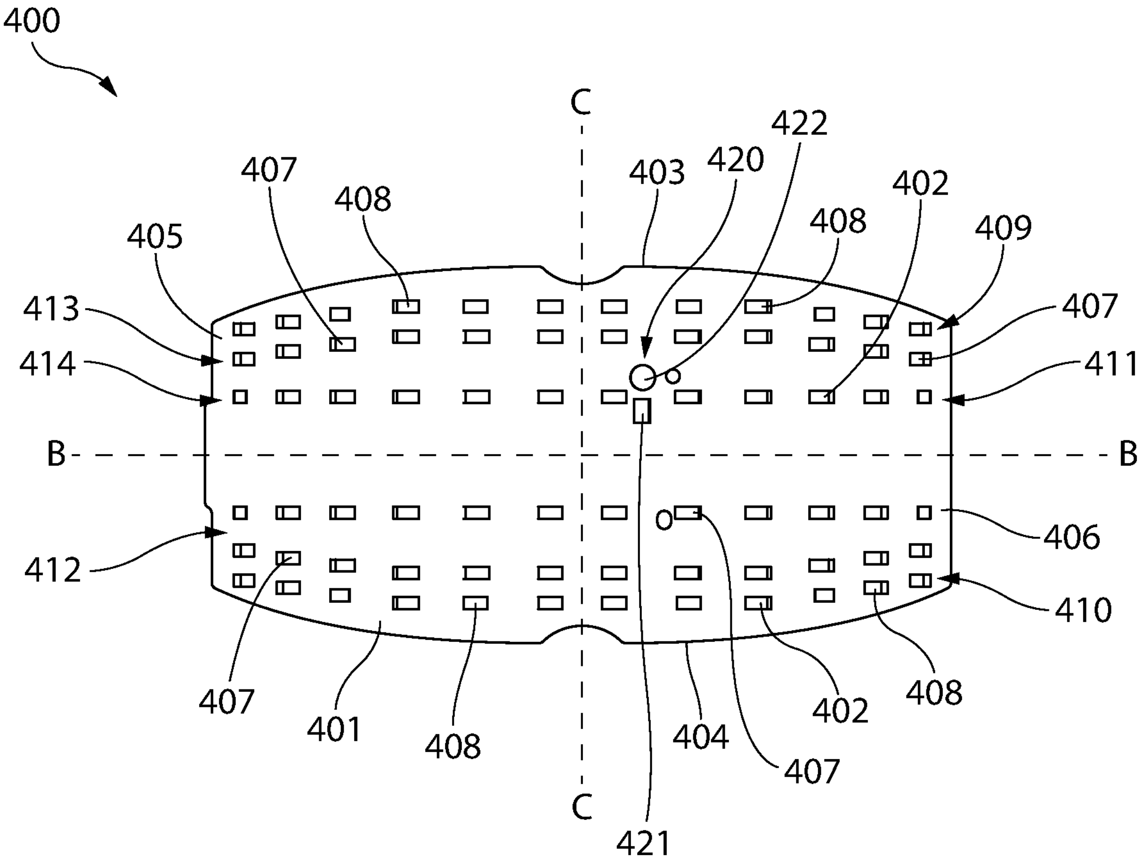
FIG. 6 is a front view of a lamp of the oral treatment device of FIG. 1.
Figure 7A:
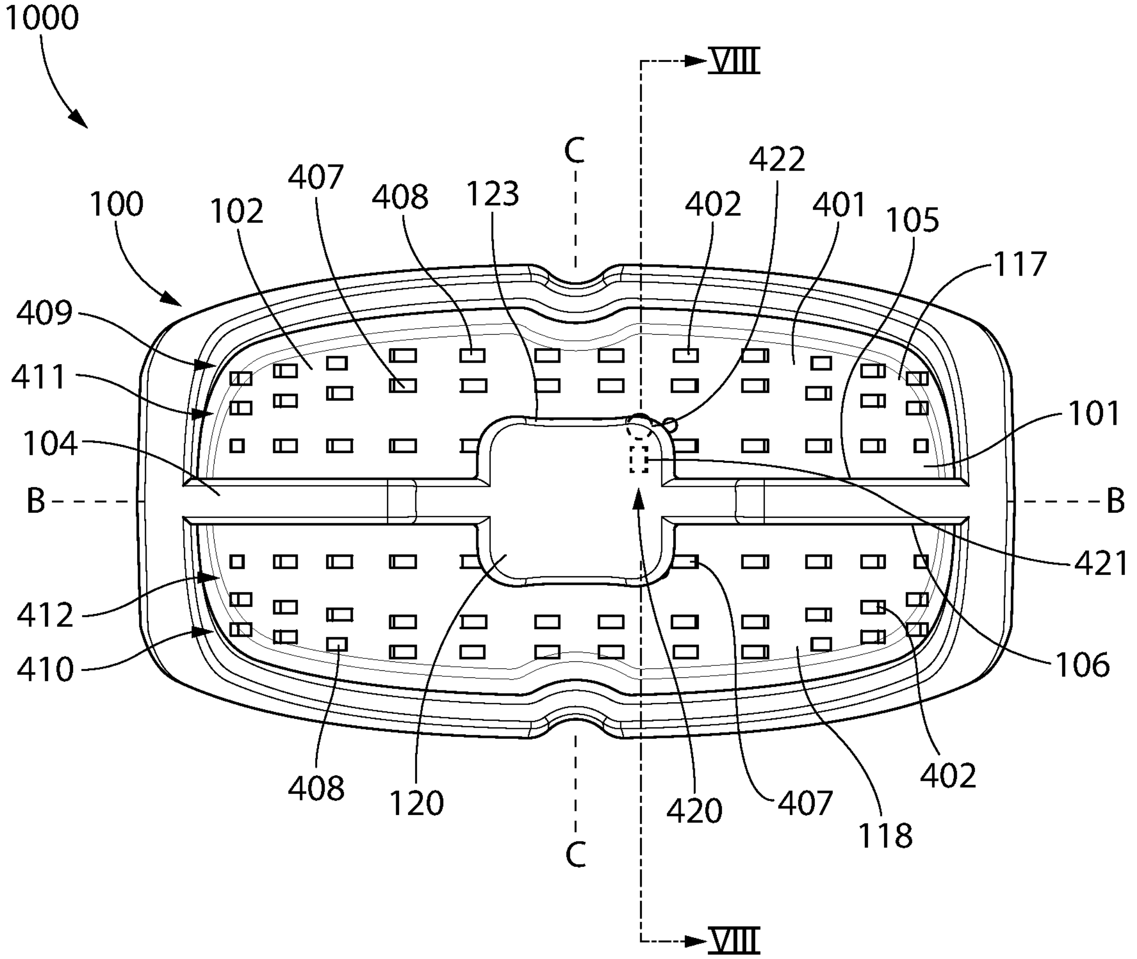
FIG. 7A is a front view of the oral treatment device of FIG. 1 with the lamp of FIG. 6 visible through a front surface thereof.

Referring to FIGS. 6 and 7A, the lamp 400 will be further described. While FIG. 7A illustrates the lamp 400 and the light emitters thereon as being visible through the arcuate wall 101 of the intraoral mouthpiece 100, this is not necessarily the situation with the actual device and is only illustrated this way for clarity of description and understanding. Thus, when not activated, the light emitters may not be able to be seen through the arcuate wall 101 formed by the front surface 321 of the lens plate 320 in all embodiments, although the light emitters may be visible as shown in other embodiments.

The lamp 400 comprises the flexible sheet body 401 having a top edge 403, a bottom edge 404, a first side edge 405, and a second side edge 406. In the exemplified embodiment the flexible sheet body 401 has a rectangular shape, but the invention is not to be so limited and the shape of the flexible sheet body 401 may be modified, keeping in mind that the flexible sheet body 401 should be shaped so as to enable electromagnetic radiation to be emitted onto the outer surfaces of as many of the user's teeth as may be desired for a whitening treatment. The flexible sheet body 401 comprises a first axis B-B which is at the location where the bite platform 104 extends in the assembled oral treatment device 1000 and a second axis C-C which lies in the dental arch midline plane P-P described above.

The plurality of electromagnetic radiation emitting elements 402 comprises a plurality of first electromagnetic radiation emitting elements 407 and a plurality of second electromagnetic radiation emitting elements 408. The plurality of first electromagnetic radiation emitting elements 407 are configured to emit violet light and the plurality of second electromagnetic radiation emitting elements 408 are configured to emit red light. The violet light emitted by the plurality of first electromagnetic radiation emitting elements 407 may have a wavelength between 380 nm and 450 nm, more specifically between 400 nm and 420 nm, and still more specifically approximately 410 nm (with the term approximately equating to a difference of plus or minus 5 nm). In other embodiments, instead of violet light, the plurality of first electromagnetic radiation emitting elements 407 may be configured to emit blue light (wavelength between 440 nm and 490 nm) or indigo light (wavelength between 420 nm and 440 nm). Thus, in some embodiments the plurality of first electromagnetic radiation emitting elements 407 may be configured to emit one of violet light, indigo light, and blue light, although violet light may be preferred in some embodiments. The red light emitted by the plurality of second electromagnetic radiation emitting elements 408 may have a wavelength between 620 nm and 700 nm, more specifically between 620 nm and 650 nm, and more specifically approximately 635 nm (again, with the term approximately equating to a difference of plus or minus 5 nm). Violet light in the wavelengths noted above have been known to be effective to whiten teeth, particularly when used in conjunction with a tooth whitening composition such as one containing hydrogen peroxide or the like. Red light in the wavelengths noted above have been known to have healing capabilities, such as to alleviate gum inflammation and pain.

Thus, because the red light is intended to be emitted onto the user's gums and the violet light is intended to be emitted onto the user's teeth, the plurality of first and second electromagnetic radiation emitting elements 407, 408 are specifically located along the flexible sheet body 401 to achieve that end. That is, the plurality of second electromagnetic radiation emitting elements 408 are arranged in a first row 409 that is adjacent to the top edge 403 of the flexible sheet body 401 of the lamp 400 and a second row 410 that is adjacent to the bottom edge 404 of the flexible sheet body 401 of the lamp 400. The plurality of first electromagnetic radiation emitting elements 407 are all located between the first and second rows 409, 410 of the plurality of second electromagnetic radiation emitting elements 408 moving in a direction of the axis C-C between the top and bottom edges 403, 404 of the flexible sheet body 401. Thus, the plurality of first electromagnetic radiation emitting elements 407 comprises a first set 411 located along the upper portion 117 of the arcuate wall 101 between the first row 409 of the plurality of second electromagnetic radiation emitting elements 408 and the upper surface 105 of the bite platform 104. Furthermore, the plurality of first electromagnetic radiation emitting elements 407 comprises a second set 412 located along the lower portion 118 of the arcuate wall 101 between the second row 410 of the plurality of second electromagnetic radiation emitting elements 408 and the lower surface 106 of the bite platform 104. This positioning aligns the second electromagnetic radiation emitting elements 408 with a user's gums and the first electromagnetic radiation emitting elements 407 with a user's teeth when the intraoral mouthpiece 100 is positioned in the user's mouth. It should be appreciated that as used herein the term row is not limited to only a straight row, but can include curved rows or the like.

In the exemplified embodiment, the first set 411 of the plurality of first electromagnetic radiation emitting elements 407 are arranged in two rows and the second set 412 of the plurality of first electromagnetic radiation emitting elements 407 are arranged in two rows. However, the invention is not to be so limited in all embodiments. That is, the plurality of first electromagnetic radiation emitting elements 407 could be positioned randomly along the region where they are located (i.e., between the second electromagnetic radiation emitting elements 408 and the bite platform 104). In other embodiments, the plurality of first electromagnetic radiation emitting elements 407 could be positioned in a single row or more than two rows along each of the upper and lower portions 117, 118 of the arcuate wall 101.

Looking just at the flexible sheet body 401 shown in FIG. 6, there is a space in the direction of the axis C-C between the first and second sets 411, 412 of the plurality of first electromagnetic radiation emitting elements 407. This space has a height (measured in the direction of the axis C-C) which is greater than the thickness of the bite guard 104. Thus, when the oral treatment device 1000 is assembled, the bite guard 104 does not block or cover any of the electromagnetic radiation emitting elements 402 and the light emitted from each is therefore capable of being emitted onto the user's teeth and gums.

As noted above, the lamp 400 also comprises the color measurement sensor 420, which comprises the light emitter 421 and the light receiver 422. The light emitter 421 may be an LED, such as a white LED, in some embodiments. However, the light emitter 421 may be any of the different types of light sources described above. The light receiver 422 may be a device that can capture three primary colors of RGB using an organic semiconductor. The light receiver 422 may be configured to express the tooth color as three values: L* for perceptual lightness, and a* and b* for the four unique colors of human vision: red, green, violet, and yellow. The light receiver 422 and or a processer operably coupled thereto can utilize the received reflected light information and determine a tooth color value therefrom. Thus, changes in color may be calculated using the CIE L*a*b* color difference equation, or using other color detection equations and/or techniques.

When the color measurement sensor 420 is activated, the light emitter 421 flashes a white light towards the user's teeth that are positioned adjacent to the arcuate wall 101. A portion of the light that reflects from the user's teeth is then received by the light receiver 422. The light receiver 422 uses the reflected light to generate tooth color data (a tooth color value) or information. As discussed below, the light receiver 422 may transmit the tooth color data or information to an external electronic device for processing and providing the user with information related to the tooth color in a easily understandable way. Alternatively, the oral treatment device 1000 may comprise processor(s) and a display for processing the color data and presenting it to the user. As discussed above, it is important to ensure that the light receiver 422 is receiving light reflected from the same spot on the same tooth of the user each time that the color measurement is taken to increase accuracy in the results provided to the user. The alignment feature 120 of the intraoral mouthpiece 100 helps to facilitate this consistency and accuracy by positioning the measured tooth at the same location relative to the color measurement sensor 420 each time the intraoral mouthpiece 100 is inserted into the user's mouth.

In the exemplified embodiment, the light emitter 421 and the light receiver 422 of the color measurement sensor 420 are located along or among the first set 411 of the plurality of first electromagnetic radiation emitting elements 407. That is, the light emitter 421 and the light receiver 422 are located along the upper portion 117 of the arcuate wall 101 between the first row 409 of the plurality of second electromagnetic radiation emitting elements 408 and the bite platform 104. To be more specific, the first set 411 of the plurality of first electromagnetic radiation emitting elements 407 comprises an upper row 413 and a lower row 414. The light emitter 421 and the light receiver 422 are located generally along the lower row 414 to one side of the second axis C-C. In fact, the light emitter 421 and the light receiver 422 are located between the first two of the second electromagnetic radiation elements 408 that are above the bite platform 104 and immediately to the right of the second axis C-C. This positioning places the light emitter 421 and the light receiver 422 into alignment with the user's central incisor, which is the tooth that is preferred for the color measurement as described herein. However, it should be noted that the oral treatment device 1000 may be rotated 180° about the longitudinal axis A-A so that the color measurement sensor 420 is aligned with the user's lower teeth. Thus, if the user's top incisor is a tooth implant or missing, the user can flip the oral treatment device 1000 so that the color measurement is taken from the user's bottom incisor. Thus, with just a single color measurement sensor, there is flexibility in the particular tooth being measured for color. Of course, multiple color measurement sensors may be included as has been described herein.

Figure 8:
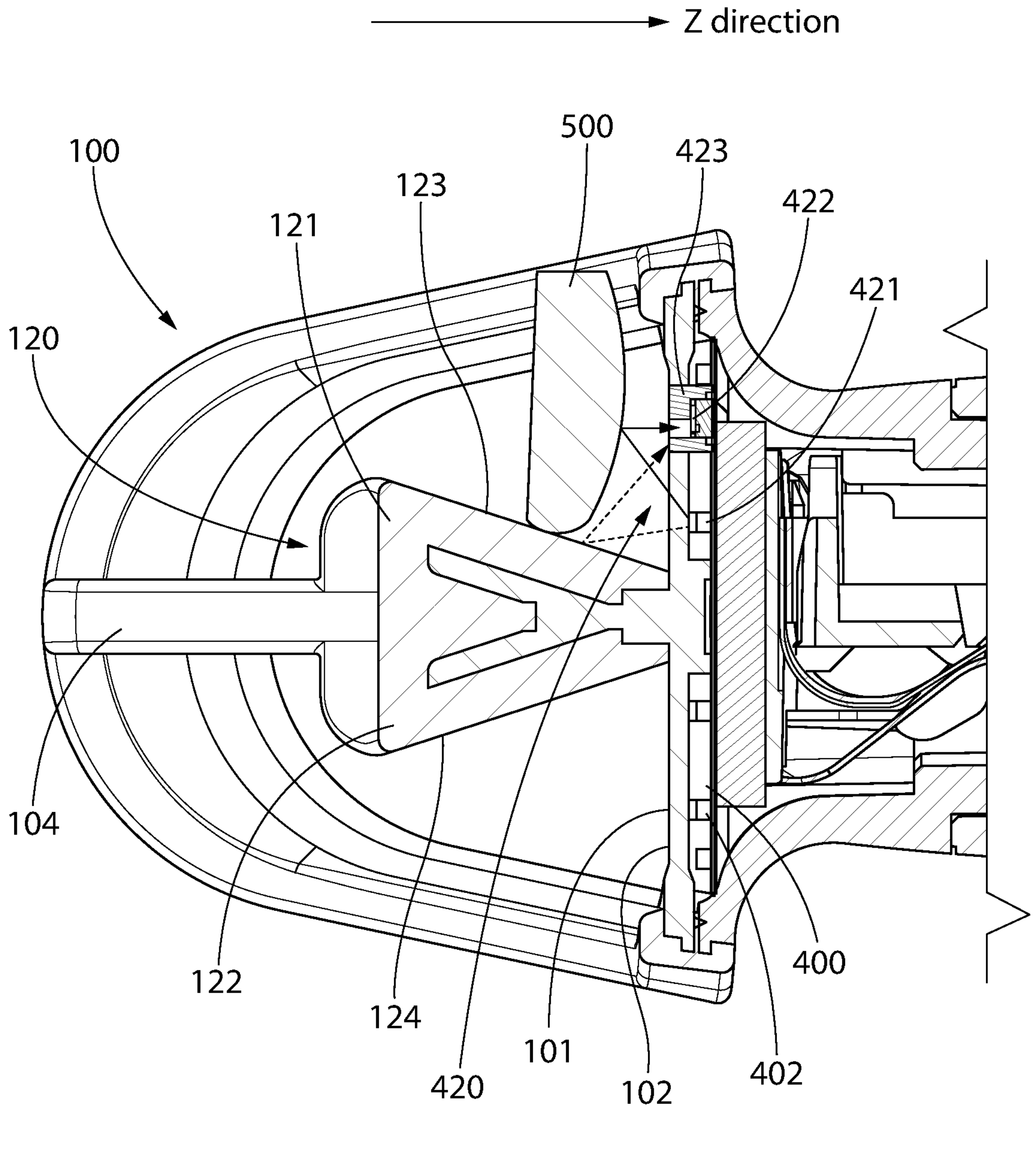
FIG. 8 is a schematic cross-sectional view taken along line VIII-VIII of FIG. 7A illustrating a color measurement sensor activated to determine a color value associated with a user's tooth.

The light emitter 421 and the light receiver 422 are positioned in vertical alignment with one another, with the light receiver 422 being positioned immediately above the light emitter 421. This positioning has been found to be reliable based on the manner in which light reflects off of a tooth due to the tooth surface contours and shape. However, the light emitter 421 and the light receiver 422 could be positioned with the light emitter 421 above the light receiver 422, or in a side-by-side adjacent manner in other embodiments. Moreover, in the exemplified embodiment at least a portion of the light emitter 421 is located between the first electromagnetic radiation emitting elements 407 in the lower row 414 and the bite platform 104. Thus, the light emitter 421 is positioned near the bite platform 104, and is configured to emit light onto a lower portion of the tooth, and specifically the central incisor. The lower part of the tooth, and specifically the central incisors, is the part that is most often visible to others when people speak, breath, or simply sit or stand in a relaxed manner. Thus, the color measurement sensor 420 is designed to take color measurements from a lower portion, more specifically a lower one-half or a lower one-fourth portion of the central incisor, to provide the user with an accurate understanding of the color of the part of the tooth that is most often seen by others. As best seen in FIG. 8, the light emitter 421 is positioned quite close to the top surface 123 of the alignment feature 120, with the light emitter 421 being between 0.5 mm and 3 mm away from the top surface 123 of the alignment feature 120 where the alignment feature 120 meets the concave inner surface 102 of the arcuate wall 101.

As seen in FIG. 7A, the light emitter 421 and the light receiver 422 of the color measurement sensor 420 are positioned along the arcuate wall 101. That is, the light emitter 421 and the light receiver 422 are positioned behind the arcuate wall 101, but in alignment therewith. The light emitter 421 and the light receiver 422 of the color measurement sensor 420 are located behind the alignment feature 120 in the assembled oral treatment device 1000. Thus, the light emitter 421 and the light receiver 422 are depicted using dashed lines or ghost lines to indicate their positioning behind the alignment feature 120. The light emitter 421 and the light receiver 422 are in alignment with the alignment feature 120 such that the light emitter 421 and the light receiver 422 both lie in a plane that is perpendicular to the upper and lower surfaces 105, 106 of the bite platform 104 and that intersects the alignment feature 120. However, the light emitter 421 and the light receiver 422 are offset from the dental arch midline plane P-P to place the light emitter 421 and the light receiver 422 into alignment with the user's central incisor rather than with the space between the user's central incisors when the intraoral mouthpiece 100 is positioned in the user's mouth. Again, the color measurement sensor 420 is positioned above the bite platform 104 to take color measurements from the central incisor of the maxillary teeth since the maxillary teeth are more often visible to others than the mandibular teeth. The oral treatment device 1000 could be rotated 180° so that the color measurement sensor 420 is positioned below the bite platform 104 (relative positioning) to take the color measurement from one of the central incisors of the mandibular teeth.

While the light emitter 421 and the light receiver 422 are located behind the alignment feature 120, due to the sloped nature of the top surface 123 of the alignment feature 120, the alignment feature 120 does not actually block the light emitter 421 and the light receiver 422 relative to the user's central incisor. Specifically, FIG. 8 illustrates a cross-sectional view through line VIII-VIII of FIG. 7A with the intraoral mouthpiece 100 positioned in a user's mouth so that the user's central incisor 500 is resting atop of the top surface 123 of the alignment feature 120. The light emitter 421 and the light receiver 422 are exposed to the surface of the tooth (e.g., central incisor) 500, meaning that no structure is blocking light from being emitted from the light emitter 421 onto the tooth 500 and being reflected from the tooth 500 to the light receiver 422. When activated, the light emitter 421 flashes a light that is emitted onto the tooth 500. Some of the light reflects off of the tooth 500 and off of the top surface 123 of the alignment feature 120, but is not received by the light receiver 422. That is, the light receiver 422 only has a small opening for receiving reflected light.

In one embodiment, the light receiver 422 may be positioned behind a baffle 423 with an opening 424 therethrough. The opening 424 may be approximately 1.25 mm or less in diameter. The light emitter 421 may be located approximately 4 mm below the opening 424. The reflected light can only reach the light receiver 422 if it is angled and oriented to pass through the opening 424 in the baffle. This further helps to ensure that the reflected light being received by the light receiver 422 is reflecting from the same spot on the tooth 500 each time the color measurement sensor 420 is activated. This also avoids the situation where the light being reflected from the alignment feature 120 is received by the light receiver 422, which could create improper measurement values. While FIG. 8 illustrates the baffle 423 extending through the lens plate 320, this is not required in all embodiments and the baffle 423 may be positioned behind the lens plate 320 in other embodiments.

Still referring to FIG. 8, it should be appreciated that when the user inserts the intraoral mouthpiece 100 into his or her mouth, the alignment feature 120 will encourage the user to position the intraoral mouthpiece 100 at the same location with each insertion. Specifically, the alignment feature 120 will encourage the user to insert the intraoral mouthpiece 100 the same distance into the mouth so that the distance between the tooth 500 and the color measurement sensor 420 (in the Z direction of the Cartesian coordinate system described previously) is the same each time that the intraoral mouthpiece 100 is positioned in the mouth. The sensor measurement result is dependent upon the reflection angle of the presented tooth surface. Thus, it should be appreciated that it is important to make sure that the tooth is at the same position relative to the color measurement sensor 420 so that the color measurement is taken from the same spot on the tooth 500 each time the color measurement sensor 420 is activated. If the distance between the tooth 500 and the color measurement sensor 420 is different for different insertions and different color measurement activations, then the color measurement may be taken from different spots on the tooth which could have different color values due to differences in reflection angle of the tooth 500. The alignment feature 120 has been found to encourage users to consistently position the intraoral mouthpiece 100 in the mouth at the same location in the Z direction.

The exemplified embodiment is described herein whereby the alignment feature 120 is configured to ensure that each time the intraoral mouthpiece is positioned into a mouth of a user, a tooth of the user is located at the same distance from the concave front surface 102 of the arcuate wall 101, and hence also from the color measurement sensor 420. Of course, there is some fluctuation that may occur because there remains a dependence on the user to consistently position the intraoral mouthpiece 100 into the mouth each time. Thus, while the term "the same distance" has been used, it should be appreciated that this may include a small tolerance of, for example, 1 mm in the Z direction. When a user has multiple colors or shades of color on a single tooth, the color tends to change gradually moving across the surface. Thus, a small tolerance in the positioning of the intraoral mouthpiece 100 in the mouth in the Z direction should not have a significant impact on the color value obtained by the color measurement sensor 420 over multiple successive measurements.

Referring briefly to FIG. 9, the oral treatment device 1000 is illustrated in operable communication with an electronic device 900. In the exemplified embodiment, the electronic device 900 is a smart phone, but the electronic device 900 could take on other forms such as being a tablet, a computer, a smart watch, or the like in different embodiments. The electronic device 900 may be connected to the oral treatment device 1000 using a hard wire connection. However, in the exemplified embodiment the electronic device 900 is wirelessly connected to the oral treatment device 1000. Such a wireless connection may be achieved using Bluetooth, Wi-Fi, Zigbee, or the like. As noted above, the control circuit 250 or the oral treatment device 1000 may comprise a Bluetooth module or a Wi-Fi module which may communicate with the same component of the electronic device 900. The electronic device 900 comprises a display screen 901 on which the electronic device 900 may display information to the user, including information about tooth color and tooth color changes over time.

As noted above, the oral treatment device 1000 may be powered on via the actuator 245 in some embodiments. However, electromagnetic radiation emitting elements 407, 408 and the color measurement sensor 420 of the oral treatment device 1000 may be activated using the electronic device 900. Thus, the electronic device 900 may be configured with a software application (app) downloaded thereon. When the software application is launched on the electronic device 900 and the electronic device 900 is in operable communication with the oral treatment device 1000, the electronic device 900 may be capable of controlling the activation of the electronic components of the oral treatment device 1000. Thus, a user can interact with and/or touch the touch screen of the electronic device 900 to activate the color measurement sensor 420 and/or to activate the plurality of first electromagnetic radiation emitting elements 407 and/or the plurality of second electromagnetic radiation emitting elements 408. The user may be able to activate each of the aforementioned electronic components with distinct activation protocols, or a single activation may cause the electronic components to be activated in a desired sequence (for example, the color measurement sensor 420 being activated first, followed by the plurality of second electromagnetic radiation emitting elements 408, followed by the plurality of first electromagnetic radiation emitting elements 407).

In some embodiments, it is advantageous to facilitate activation of the color measurement sensor 420 with the electronic device 900 and not via the actuator 245 on the housing 201 of the oral treatment device 1000. This is because if the actuator 245 were used to activate the color measurement sensor 420, the action of the user applying a force onto the actuator 245 (i.e., power button) may cause the oral treatment device 1000 to move/tilt in the Y-axis direction. This will result in the color measurement sensor 420 taking color measurements from inconsistent positions on the tooth depending on how hard the actuator 245 is depressed and/or how much the oral treatment device 1000 moves during the activation. By having the user activate the color measurement sensor 420 with the external electronic device 900 which is a separate and distinct device from the oral treatment device 1000, the oral treatment device 1000 can me maintained in a stable and consistent position while the color measurement is being taken.

The electronic device 900 may remain in communication with the oral treatment device 1000 so that the oral treatment device 1000, and specifically the color measurement sensor 420 thereof, may transmit data to the electronic device 900 related to the color value of the tooth as measured by the color measurement sensor 420. The electronic device 900 may then be configured to convert the color value into information that is valuable to the user, as described in some detail below. In some embodiments, the oral treatment device 1000 may comprise a memory for storing measured tooth color values, and may transmit all such stored tooth color values to the electronic device 900 once communication is established between the oral treatment device 1000 and the electronic device 900.

Referring to FIGS. 7B, 7C, 8, and 9 concurrently, a brief description of the operation of the oral treatment device 1000 will be described in accordance with an embodiment of the present invention. First, the intraoral mouthpiece 100 of the oral treatment device 1000 is inserted into the user's mouth to obtain a baseline color measurement from the user, and specifically from the user's central incisor. During this first insertion of the intraoral mouthpiece 100 into the user's mouth, the user's teeth are not coated with any composition, nor is there any composition on the concave front surface 102 of the arcuate wall 101. As discussed in detail herein, the alignment feature 120 of the intraoral mouthpiece 100 encourages the user to insert the intraoral mouthpiece 100 the same distance in the Z-direction each time the intraoral mouthpiece 100 is positioned in the mouth. This ensures that the tooth being measured by the color measurement sensor 420 is located at the same position relative to the color measurement sensor 420 (and/or relative to the concave front surface 102 of the arcuate wall 101) each time the color measurement is taken from the tooth.

Next, the color measurement sensor 420 may be activated to take a color measurement from the tooth 500. Alternatively, the color measurement sensor 420 may be activated wirelessly using the electronic device 900. Specifically, the software application launched on the electronic device 900 may have an icon or button or location on the display thereof for the user to press to activate the color measurement sensor 420 to take a color measurement. Upon activation of the color measurement sensor 420, the light emitter 421 emits a flash of light towards the tooth 500. The light reflects off of the tooth 500 and some of the reflected light is received by the light receiver 422. As noted above, because the alignment feature 120 ensures that the tooth 500 is located the same distance from the color measurement sensor 420 each time the intraoral mouthpiece 100 is inserted into the user's mouth, the color measurement is taken from the same spot (possibly within a tolerance as noted above) on the tooth each time a color measurement is taken. The color measurement data may then be stored in a memory of the oral treatment device 1000 and/or transmitted to the electronic device 900 and displayed to the user in a visual representative format. The color measurement data may also be stored in the memory of the electronic device 900. The first color measurement taken by the user during a particular treatment protocol is used as a baseline measurement against which all later color measurements is compared for purposes of illustrating to the user the color change over time. If a user completes a treatment protocol and at a later date wants to start a new treatment protocol, the user can take another initial baseline measurement for each treatment protocol by properly interacting with the software application on the electronic device 900. By taking a baseline measurement and then continuing to take daily measurements during the treatment protocol, the user can obtain a quantitative reference of the change in color relative to the baseline over time.

Once the color measurement has been obtained, the user may use the oral treatment device 1000 to perform a gum inflammation treatment and/or to perform a whitening treatment. The invention will be described in a situation whereby the user intends to perform both the gum inflammation treatment and the whitening treatment. However, it should be appreciated that the user could omit one or both of these steps as desired.

After taking the color measurement from the tooth, the user may remove the intraoral mouthpiece 100 from the mouth. This will enable the user to apply a whitening composition onto his or her teeth. Thus, while the emission of violet light onto the teeth may facilitate whitening thereof, this whitening is enhanced when a tooth whitening composition is first applied onto the teeth. The tooth whitening composition may be applied directly onto the teeth using any of various applicators, such as by painting the composition onto the teeth, placing a tray with the composition thereon into the mouth, or the like. The whitening composition may be any composition currently known for tooth whitening purpose, including those that comprise varying weight percentages of hydrogen peroxide (from 0.1 wt % to 10 wt %, or the like).

Figure 7B:
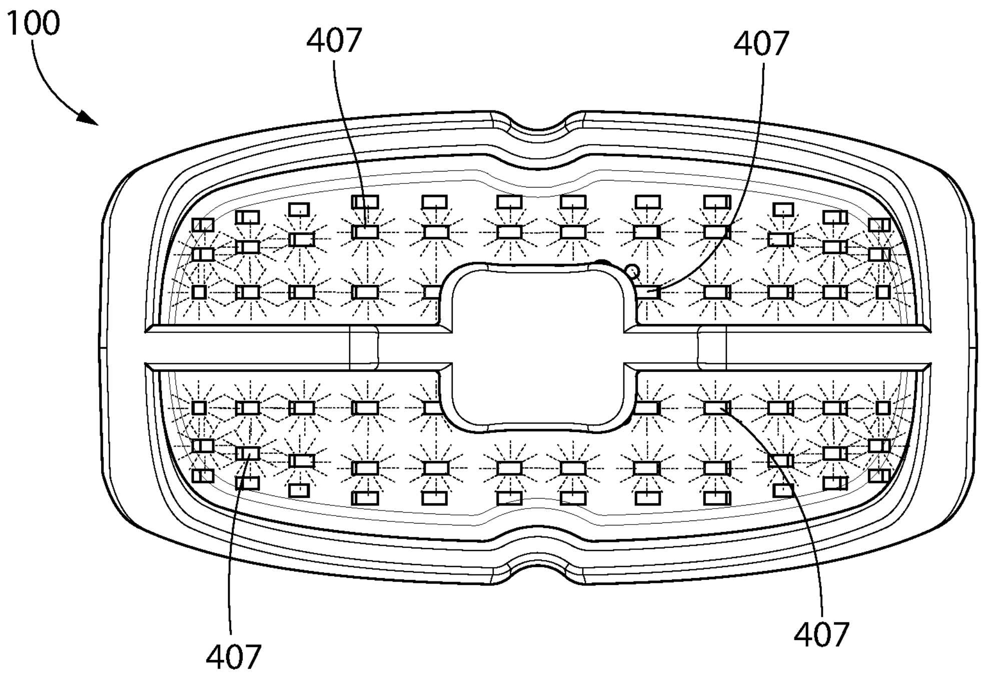
FIG. 7B is the front view of the oral treatment device of FIG. 7A with a plurality of first electromagnetic radiation emitting elements activated.
Figure 7C:
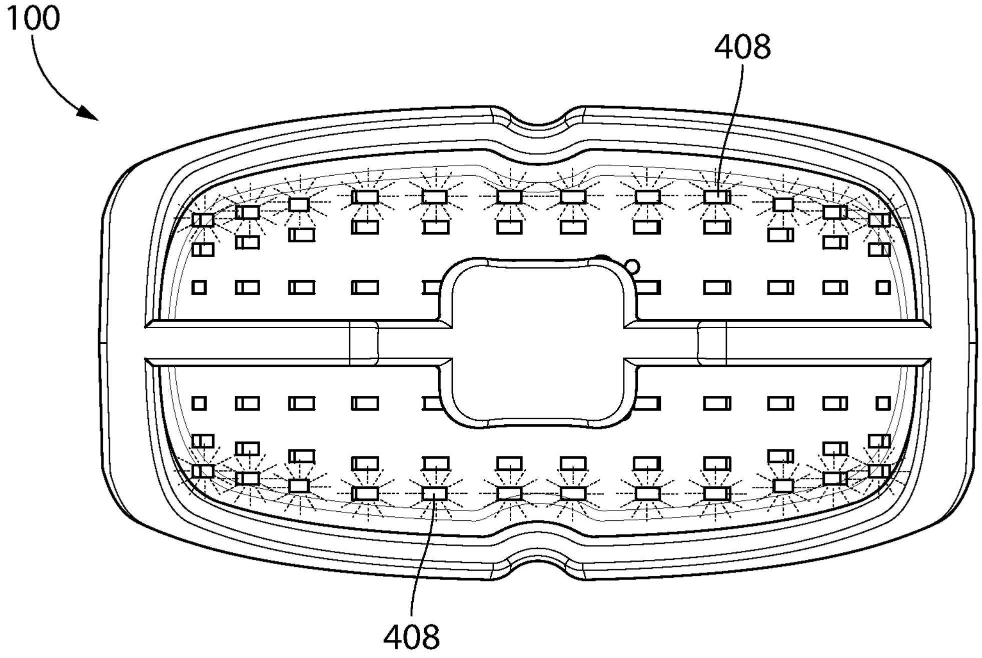
FIG. 7C is the front view of the oral treatment device of FIG. 7A with a plurality of second electromagnetic radiation emitting elements activated.

After applying the tooth whitening composition to the teeth, the intraoral mouthpiece 100 is inserted back into the user's mouth. The user may be directed to wait for a certain amount of time (i.e., 5 minutes or 10 minutes or the like) after application of the tooth whitening composition onto the teeth before inserting the intraoral mouthpiece 100 into the mouth in some embodiments, although this may not be required or necessary in all embodiments. Next, as shown in FIG. 7B, the user may activate the plurality of first electromagnetic radiation emitting elements 407, which are configured to emit violet light onto the teeth of the user. As noted above, this activation of the plurality of first electromagnetic radiation emitting elements 407 may be achieved via user interaction on the electronic device 900. Having violet light emitted onto the teeth that are pre-coated with the tooth whitening composition increases and enhances the whitening benefit achieved. The plurality of first electromagnetic radiation emitting elements 407 may be activated for a first predetermined period of time, which may be between 5 and 20 minutes, more specifically between 10 and 20 minutes, more specifically between 15 and 20 minutes, or the like. The length of time may be longer than 20 minutes in some embodiments as well.

After expiration of the first predetermined period of time, the plurality of first electromagnetic radiation emitting elements 407 may be automatically deactivated. Alternatively, a user may press a button on the oral treatment device 1000 or interact with the electronic device 900 to deactivate the plurality of first electromagnetic radiation emitting elements 407. Once the plurality of first electromagnetic radiation emitting elements 407 have been deactivated, the user can remove the intraoral mouthpiece 100 from his or her mouth.

Next, the user may leave the tooth whitening composition on the teeth for a period of time. For example, the tooth whitening composition may be one that is intended to be left on the teeth overnight, or for a certain timeframe (one hour, two hours, three hours, four hours, or more). Thus, the user may go to sleep without removing the tooth whitening composition from the teeth so that the tooth whitening composition can continue to whiten the teeth during the overnight hours. In such a situation, the user will remove the tooth whitening composition from the teeth the next morning, by brushing the teeth in the conventional manner. In other embodiments, the user may desire to remove the tooth whitening composition immediately after removing the oral treatment device 1000 from the mouth, although this may depend on the particular type of tooth whitening composition used.

In any case, after the tooth whitening composition has been removed from the teeth, the user may want to complete a gum treatment. Thus, the user may insert the oral treatment device 1000 back into the user's mouth, and activate the plurality of second electromagnetic radiation emitting elements 408, as shown in FIG. 7C. The user may activate the plurality of second electromagnetic radiation emitting elements 408 by interacting with the electronic device 900 or pressing a button directly on the oral treatment device 1000.

As noted above, the plurality of second electromagnetic radiation emitting elements 408 are configured to emit red light, which can be used for healing or to alleviate pain. Upon activation, the plurality of second electromagnetic radiation emitting elements 408 may be configured to remain activated for a second predetermined period of time. The second predetermined period of time may be between 3 and 10 minutes, more specifically between 3 and 8 minutes, and more specifically between 3 and 5 minutes. The second predetermined period of time may be longer than 10 minutes in some embodiments as well. The plurality of second electromagnetic radiation emitting elements 408 may deactivate automatically after expiration of the second predetermined period of time. In other embodiments, once the plurality of second electromagnetic radiation emitting elements 408 are activated, they may remain activated until the user deactivates them (such as by pressing a button or interacting with the software application on the electronic device 900).

In some embodiments, prior to the activation of the plurality of second electromagnetic radiation emitting elements 408, the user may apply a healing or treatment composition or ointment onto the gums, which may work together with the red light of the plurality of second electromagnetic radiation emitting elements 408 for gum healing purposes. Moreover, in some embodiments the plurality of first and second electromagnetic radiation emitting elements 407, 408 may be configured for simultaneous activation, so that the red light is applied to the gums and the violet light is applied to the teeth at the same time. This may be an alternative or additional treatment cycle option that can be selected by the user, or it may be the preferred treatment cycle.

Finally, after the gum treatment with the red light, the user may take another color measurement of the teeth with the color measurement sensor 420. Thus, the user may place the intraoral mouthpiece 100 back into the mouth and activate the color measurement sensor 420. The oral treatment device 1000 will send data indicative of the color measurement to the software application on the electronic device 900. The electronic device 900 may then display the color measurement obtained during this second measurement with a comparison to the baseline measurement taken from the initial color measurement prior to starting the treatment protocol and any intervening color measurements taken so that the user can track his or her whitening progress. It should be noted that the user may omit the red light treatment in some embodiments if there is no desire to heal or treat the gums.

The next time that the user performs a treatment (such as the next night), the user will perform all of these steps again. That is, the user will take a first color measurement, then apply the whitening composition to the teeth, then emit the violet light onto the teeth, then the user will sleep. The next morning, the user will remove the tooth whitening composition from the teeth and emit the red light onto the gums for healing. Finally, the user will take another color measurement. For this second treatment, the first and second color measurements will still be compared to the initial baseline measurement taken the prior day (or on the initial treatment day). The user will be able to see changes over time and changes relative to the baseline measurement taken on the first day of the treatment protocol. While day to day color changes may be minimal and not noticeable to the naked eye, the color change over the course of several days of treatment will be significant, and this will encourage the user to continue the treatment protocol.

While a particular order of operations has been described herein, and the described order is preferred, the invention is not to be so limited in all embodiments. The software application on the electronic device 900 may provide the user with the opportunity to determine the order of operations (or the user may be able to actuate different buttons associated with activation of the different electronic components in a preferred order). The oral treatment device 1000 may be configured so that the plurality of first and second electromagnetic radiation emitting elements 407, 408 may be activated simultaneously in some embodiments. One benefit in taking the color measurement before the tooth whitening is that the color measurement can be taken before coating the teeth with the whitening composition. If the user takes the color measurement after tooth whitening, the user will need to clean the whitening composition from the teeth prior to taking the color measurement.

Figure 10:
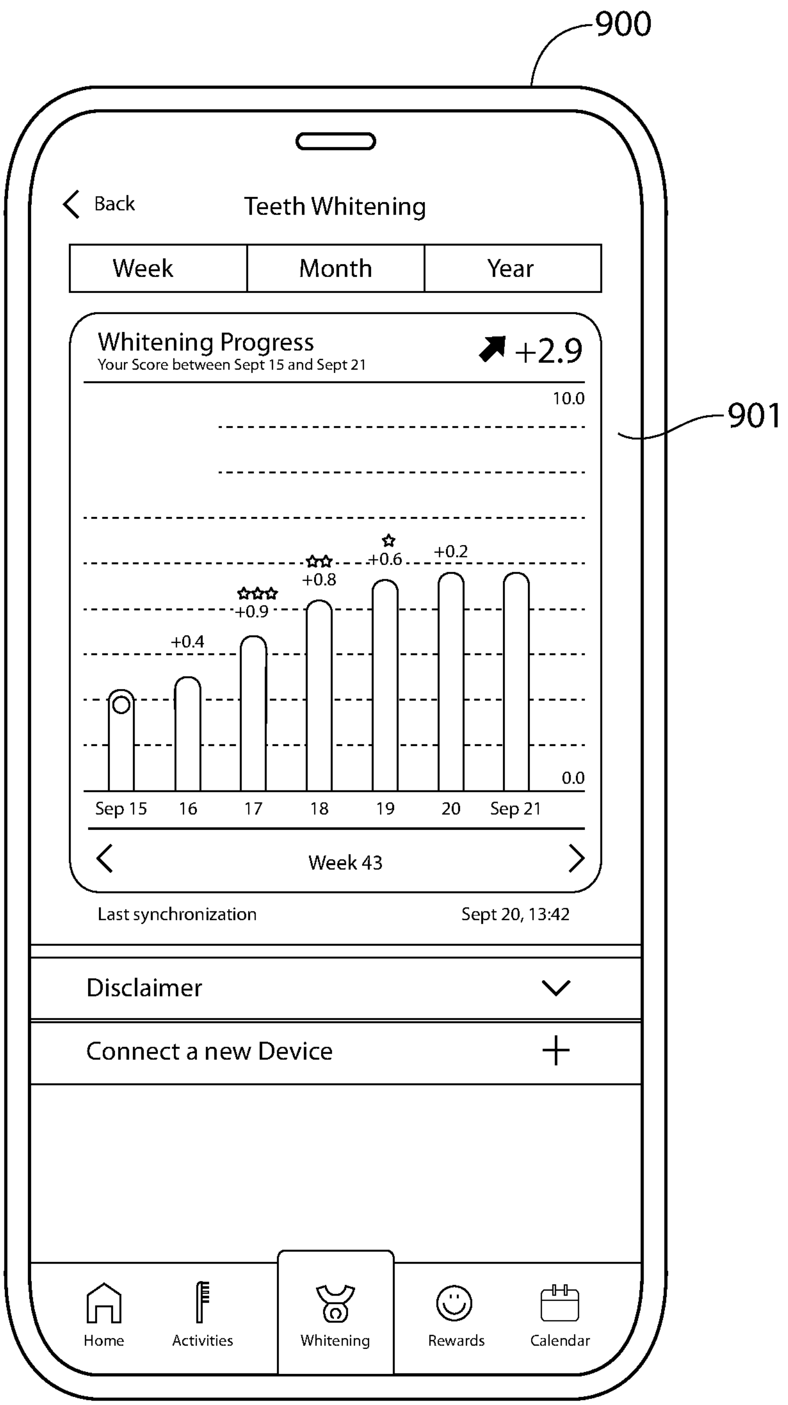
FIG. 10 is a front view of the electronic device of FIG. 9 running a software application to display a graphical representation indicating a tooth color change over time.

Referring to FIG. 10, an example of a visual representation of information that may be displayed on the display screen 901 of the electronic device 900 when the teeth whitening software application is launched is illustrated. When the user launches the software application on the electronic device 900, the user will have the ability to view a chart or a graph or the like which contains information indicative of the change in tooth color over time. In FIG. 10, the user has selected the "whitening" icon at the bottom, which results in the display shown in FIG. 10. The user can select the "Home" icon the "Activities" icon, the "Rewards" icon, or the "Calendar" icon to see other representations on the display screen 901. As described above, the color measurement sensor 420 of the oral treatment device 1000 takes color measurements from one of the user's teeth each time that the user inserts the intraoral mouthpiece 100 into the mouth and activates the color measurement sensor 420. Furthermore, the color measurement sensor 420 transmits data indicative of the measured color to the software application on the electronic device 900. The software application then sorts the color measurement data and arranges it into a chart or graph that is user friendly so that the user can have a visual representation of the color changes occurring over time. A chart or graph is not required in all embodiments, and a listing of dates and measurement values could be provided in other ways.

FIG. 10 illustrates a bar graph which illustrates color measurements taken on the tooth for seven consecutive days. The chart illustrates the tooth color by the length of the bars in the bar graph (smaller bar is darker color and taller bar is lighter color). The chart also provides a numerical value associated with the change from one day to the next day. For example, on top of the bar for September 16, it indicates "+0.4" to indicate a change of 0.4 on the whitening scale. Such a small change would likely not be noticeable to the user simply from viewing his or her teeth in the mirror due to the concept of the just noticeable different. If a user cannot see the change in color over time, the user may become frustrated and stop using the product. By providing the user with the graphical indication containing tooth color information, the user can readily see that the treatment is working and the user's tooth color is changing.

Furthermore, due to the intraoral mouthpiece 100 including the alignment feature 120, the user can be confident that the tooth color measurements each day are being taken from the same spot on the same tooth. Thus, the graphical representation of the change in tooth color is representative of an actual change in color, not a change in the location or spot at which the measurement is being taken from one day to the next. Again, this should provide the user with confidence that the whitening treatment is working, which will encourage the user to maintain compliance with the treatment regimen.

The description of the top and bottom surfaces 123, 124 of the alignment feature 120 being inclined upwardly and downwardly is relevant when the oral treatment device 1000 is positioned with the axis A-A along which the handle 200 extends is horizontal. When so oriented, the top surface 123 is inclined or sloped in an upward directly (i.e., towards the sky and away from the ground or floor) and the bottom surface 124 is inclined or sloped in a downward direction (i.e., towards the ground or floor and away from the sky). Furthermore, each of the top and bottom surfaces 123, 124 of the alignment feature 120 intersect the concave front surface 102 of the arcuate wall 101 at an acute angle.

The invention may be directed to an oral care kit which comprises the intraoral mouthpiece 100 and a tooth whitening composition. Such a tooth whitening composition may be placed within a tube or container or bottle with an applicator for applying the tooth whitening composition to the user's teeth. The intraoral mouthpiece 100 and the tooth whitening composition may be contained and sold in the same package. Furthermore, the oral care kit may also include instructions for performing tooth whitening using the intraoral mouthpiece 100 and the tooth whitening composition, such as the methods and processes and steps described herein above. Such instructions may be written on paper held within the package, may be written on the package itself, or may be accessed electronically. For example, the package or the like may contain a machine readable code, such as a QR code or other type of barcode that may be readable by an electronic device such a smartphone. A user may scan the machine readable code to open up a webpage or the like which contain instructions for use. In other embodiments, such instructions may be found on a software app that is sold with or separately from the intraoral mouthpiece 100 and/or the tooth whitening composition. Thus, instructions may be included with the kit or electronically accessible to the user.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral treatment device comprising:

an intraoral mouthpiece comprising:

an arcuate wall comprising a concave front surface; a bite platform extending from the concave front surface of the arcuate wall, the bite platform comprising an upper surface;

an alignment feature located on or adjacent to the bite platform and comprising a top surface that is elevated above the upper surface of the bite platform along an entirety of a length of the top surface of the alignment feature, wherein the bite platform terminates at a distal edge and comprises a lower surface, and wherein the top surface of the alignment feature is sloped upwardly moving in a direction from the concave front surface of the arcuate wall towards the distal edge of the bite platform; and a color measurement sensor positioned along the arcuate wall, the color measurement sensor comprising a light emitter configured to emit light onto a tooth and a light receiver configured to receive reflected light that has reflected from the tooth to determine a color value for the tooth; and wherein the alignment feature is configured to ensure that each time the intraoral mouthpiece is positioned into a mouth of a user, the tooth is located at a same distance from the color measurement sensor so that the reflected light is reflected from an identical location along the tooth when the color measurement sensor is activated.

2. The oral treatment device according to claim 1, wherein the alignment feature comprises a bottom surface that is sloped downwardly moving in the direction from the concave front surface of the arcuate wall towards the distal edge of the bite platform, and wherein the top and bottom surfaces of the alignment feature are located on opposite sides of the bite platform.

3. The oral treatment device according to claim 1, wherein the top surface of the alignment feature extends from the concave front surface of the arcuate wall to a distal surface of the alignment feature, the distal surface of the alignment feature being flush with the distal edge of the bite platform.

4. The oral treatment device according to claim 1, wherein the alignment feature comprises a first side surface that extends from the top surface of the alignment feature to the upper surface of the bite platform and a second side surface that extends from the top surface of the alignment feature to the upper surface of the bite platform, each of the first and second side surfaces being rounded.

5. The oral treatment device according to claim 1, wherein a height of the alignment feature measured from the upper surface of the bite platform to the top surface of the alignment feature increases continuously moving from the arcuate wall to a distal edge of the bite platform.

6. The oral treatment device according to claim 1 wherein the alignment feature is a wedge shaped member that protrudes from at least one of the upper surface and the lower surface of the bite platform.

7. The oral treatment device according to claim 1 wherein the alignment feature is configured such that, when the intraoral mouthpiece is positioned in the mouth of the user, the tooth rests atop the alignment feature, and wherein the tooth is a central incisor.

8. The oral treatment device according to claim 1 wherein the bite platform comprises the upper surface and the lower surface, and wherein the light emitter and the light receiver of the color measurement sensor are aligned with the alignment feature such that the light emitter and the light receiver lie in a plane that is perpendicular to the upper and lower surfaces of the bite platform and the intersects the alignment feature.

9. The oral treatment device according to claim 1 further comprising a lamp positioned adjacent to the arcuate wall and configured to emit electromagnetic radiation onto oral surfaces when the intraoral mouthpiece is positioned within the mouth of the user and activated, the lamp comprising a plurality of electromagnetic radiation emitting elements and the color measurement sensor.

10. The oral treatment device according to claim 9 wherein the plurality of electromagnetic radiation emitting elements of the lamp comprises:

a plurality of first electromagnetic radiation emitting elements that emit one of a violet light, an indigo light, and a blue light when activated; and a plurality of second electromagnetic radiation emitting elements that emit a red light when activated; and wherein the plurality of first electromagnetic radiation emitting elements are located between the plurality of second electromagnetic radiation emitting elements and the bite platform, the plurality of first electromagnetic radiation emitting elements being positioned so as to emit the one of the violet, indigo, and blue light onto surfaces of the user's teeth when activated, and the plurality of second electromagnetic radiation emitting elements being positioned so as to emit red light onto the user's gums when activated.

11. The oral treatment device according to claim 10 wherein upon activating the color measurement sensor while the intraoral mouthpiece is located within the mouth of the user, the color measurement sensor determines the color value for the tooth, wherein upon activating the plurality of first electromagnetic radiation emitting elements, the plurality of first electromagnetic radiation emitting elements emit the one of the blue, indigo, and violet light onto surface of the user's teeth for a first predetermined period of time, and wherein upon activating the plurality of second electromagnetic radiation emitting elements, the plurality of second electromagnetic radiation emitting elements emit the red light onto the user's gums for a second predetermined period of time.

12. An oral treatment device comprising:

an intraoral mouthpiece comprising:

an arcuate wall comprising a front surface;

a bite platform extending from the front surface of the arcuate wall, the bite platform terminating at a distal edge;

an alignment feature located on or adjacent to the bite platform, the alignment feature extending from the front surface of the arcuate wall to the distal edge of the bite platform and comprising a sloped top surface that is inclined upwardly with increasing distance from the front surface of the arcuate wall toward the distal edge of the bite platform; and a color measurement sensor aligned with the alignment feature and configured to obtain a color measurement of a tooth when the tooth is located along the alignment feature.

13. The oral treatment device according to claim 12 wherein the alignment feature comprises a distal surface that is flush with the distal edge of the bite platform.

14. The oral treatment device according to claim 12 wherein the bite platform comprises an upper surface and a lower surface, and wherein the alignment feature is a wedge shaped member that protrudes from both of the upper and lower surfaces of the bite platform so that the sloped top surface and a bottom surface of the alignment feature diverge from one another with increasing distance away from the front surface of the arcuate wall.

15. The oral treatment device according to claim 12 wherein the color measurement sensor comprises a light emitter configured to emit light onto the tooth and a light receiver configured to receive reflected light that has reflected from the tooth to obtain the color measurement of the tooth, and wherein the reflected light is reflected from an identical location along the tooth each time the intraoral mouthpiece is positioned into a mouth of a user.

16. The oral treatment device according to claim 12 further comprising a lamp positioned adjacent to the arcuate wall and configured to emit electromagnetic radiation onto oral surfaces when the intraoral mouthpiece is positioned within the mouth of the user and activated, the lamp comprising a plurality of electromagnetic radiation emitting elements and the color measurement sensor, wherein the plurality of electromagnetic radiation emitting elements of the lamp comprises:

a plurality of first electromagnetic radiation emitting elements that emit a violet light when activated; and a plurality of second electromagnetic radiation emitting elements that emit a red light when activated; and wherein the plurality of first electromagnetic radiation emitting elements are located between the plurality of second electromagnetic radiation emitting elements and the bite platform, the plurality of first electromagnetic radiation emitting elements being positioned so as to emit violet light onto surfaces of the user's teeth when activated, and the plurality of second electromagnetic radiation emitting elements being positioned so as to emit red light onto the user's gums when activated.

17. The oral treatment device according to claim 16 wherein the lamp comprises a top edge and a bottom edge, wherein the plurality of second electromagnetic radiation emitting elements comprises a first row positioned adjacent to the top edge of the lamp and a second row positioned adjacent to the bottom edge of the lamp, and wherein the plurality of first electromagnetic radiation emitting elements are all located between the first and second rows of the plurality of second electromagnetic radiation emitting elements.

18. The oral treatment device according to claim 12 wherein the top surface of the alignment feature is inclined upwardly in a direction of an axis that is parallel or coincident to a direction of a translational movement of the intraoral mouthpiece during insertion of the intraoral mouthpiece into a mouth of a user.

19. A method of obtaining a color measurement of a tooth, the method comprising:

inserting an intraoral mouthpiece into a mouth of a user, the intraoral mouthpiece comprising, an arcuate wall comprising a concave front surface;

a bite platform extending from the concave front surface of the arcuate wall, the bite platform comprising an upper surface;

an alignment feature located on or adjacent to the bite platform and comprising a top surface that is elevated above the upper surface of the bite platform along an entirety of a length of the top surface of the alignment feature, wherein the bite platform terminates at a distal edge and comprises a lower surface, and wherein the top surface of the alignment feature is sloped upwardly moving in a direction from the concave front surface of the arcuate wall towards the distal edge of the bite platform;

the alignment feature ensuring that a central incisor of the user is positioned at a same distance from a color measurement sensor of the intraoral mouthpiece each time the intraoral mouthpiece is inserted into the mouth of the user;

flashing a light onto the central incisor of the user via a light emitter of the color measurement sensor of the intraoral mouthpiece;

receiving, by a light receiver of the color measurement sensor of the intraoral mouthpiece, reflected light that has reflected from a measurement location of the central incisor of the user; and determining a color measurement value based on the reflected light received by the light receiver.

* * * * *